United States Patent [19]

Rieke

[11] Patent Number: 5,490,952
[45] Date of Patent: Feb. 13, 1996

[54] HIGHLY REACTIVE FORM OF COPPER AND REAGENTS THEREOF

[75] Inventor: Reuben D. Rieke, Lincoln, Nebr.

[73] Assignee: University of Nebraska, Nebr.

[21] Appl. No.: 872,600

[22] Filed: Apr. 23, 1992

Related U.S. Application Data

[63] Continuation-in-part of Ser. No. 692,236, Apr. 26, 1991, abandoned.

[51] Int. Cl.$^6$ .................................................. C09K 3/00
[52] U.S. Cl. ........................... 252/182.33; 252/182.12; 252/183.13
[58] Field of Search ................ 252/182.12, 183.13, 252/182.33, 345

[56] References Cited

U.S. PATENT DOCUMENTS

| | | | |
|---|---|---|---|
| 3,948,803 | 4/1976 | Carney | 585/462 |
| 4,152,303 | 5/1979 | Cohen et al. | 502/243 |
| 4,687,877 | 8/1987 | Bartley | 502/345 |

OTHER PUBLICATIONS

P. Knochel et al., *J. Org. Chem.*, 53, 2392–2394 (1988).
R. A. O'Brien et al., *Magnetic Resonance in Chemistry*, 30, 398–402 (1992).
R. D. Rieke, *Crit. Rev. Surf. Chem.*, 1, 131–166 (1991).
D. E. Stack et al., *Tetrahedron Letters*, 33, 6575–6578 (1992).
A. Alexakis et al., *Tetrahedron Lett.*, 27, 1047–1050 (1986).
E. J. Corey et al., *Tetrahedron Lett.*, 26, 6015–6018 (1985).
E. J. Corey et al., *Tetrahedron Lett.*, 26, 6019–6022 (1985).
G. W. Ebert et al., *J. Org. Chem.*, 49, 5280–5282 (1984).
G. W. Ebert et al., *J. Org. Chem.*, 53, 4482–4488 (1988).
B. H. Lipshutz et al., *J. Org. Chem.*, 54, 4977–4979 (1989).
B. H. Lipshutz et al., *J. Am. Chem. Soc.*, 112, 4063–4064 (1990).
B. H. Lipshutz et al., *J. Am. Chem. Soc.*, 112, 4404–4410 (1990).
The Merck Index, 10th Ed., Merck & Co. Pub. 1983, p. 7778.
R. A. O'Brien et al., *J. Org. Chem.*, 55, 788–790 (1990).
R. D. Rieke et al., *J. Org. Chem.*, 44, 3445–3446 (1979).
R. D. Rieke, *Energy Res. Abstr.* 10(18), Abstr. No. 37255 (1985) (Report No. DOE/ER/10603–T3).
R. D. Rieke et al., *High Energy Processes in Organometallic Chemistry*, ACS Symposium Series No. 333, ACS 1987, Ch. 14, pp. 223–245.
R. D. Rieke et al., Paper entitled "Direct formation of functionalized organocopper reagents from highly reactive copper and alkyl halides" (Abstract No. 306), presented at American Chemical Society 196th National Meeting, Los Angeles, CA, Sep. 25–30, 1988.
R. D. Rieke, *Science*, 246, 1260–1264 (1989).
R. D. Rieke et al., *Synth. Commun.*, 19, 1833–1840 (1989).
R. D. Rieke et al., *Tetrahedron*, 45, 443–454 (1989).
R. D. Rieke et al., *Synth. Commun.*, 20, 2711–2721 (1990).
D. E. Stack et al., *J. Am. Chem. Soc.*, 113, 4672–4673 (1991).
K. Takeda et al., *Bull. Chem. Soc. Jpn.*, 41, 268 (1968).
R. M. Wehmeyer et al., *J. Org. Chem.*, 52, 5056–5057 (1987).
R. M. Wehmeyer et al, *Tetrahedron Letters*, 29, 4513–4516 (1988).
T.—C. Wu et al., *J. Org. Chem.*, 52, 5057–5059 (1987).
T.—C. Wu et al., *J. Org. Chem.*, 53, 2381–2383 (1988).
T.—C. Wu et al., *Tetrahedron Letters*, 29, 6753–6756 (1988).
T.—C. Wu et al., *J. Org. Chem.*, 55, 5045–5051 (1990).
L. Zhu et al., *Tetrahedron Letters*, 32, 2865–2866 (1991).
L. Zhu et al., *J. Org. Chem.*, 56, 1445–1453 (1991).
B. T. Dawson, "I. Chemistry of Eta(5):Eta(5)–Biphenyl) (Chromium Tricarbonyl) (2) Dianions. II. Two Equivalent Reduction of Copper(I) Salts. III. A New Rieke Active Copper: Reduction of a Copper Cyanide Lithium Halide Complex (Copper Cyanide, Lithium Halide, Biphenylchromium Tricarbonyl)", Abstract of Ph.D. Thesis, The University of Nebraska—Lincoln (1992).
R. A. O'Brien, "Chemical Modification of Halogenated Polystyrene Resins Utilizing Highly Reactive Copper and Calcium and the Chemistry of Highly Reactive", Ph.D. Thesis, The University of Nebraska—Lincoln (1992).
R. M. Wehmeyer, "The Preparation and Chemistry of Active Copper, Nickel, and Zinc", Ph.D. Thesis, The University of Nebraska—Lincoln (1988).

*Primary Examiner*—Edward A. Miller
*Attorney, Agent, or Firm*—Merchant, Gould, Smith, Edell, Welter & Schmidt

[57] ABSTRACT

A novel zerovalent copper species and an organocopper reagent are disclosed. The zerovalent copper species is directly produced by reaction of a reducing agent with a combination of copper cyanide or halide and an alkali metal halide salt. The organocopper reagent resulting from the reaction of the zerovalent copper species and an organic compound having one or more stable anionic leaving groups is a stable reagent that will not significantly homocouple and under controlled conditions tolerates the presence of nitrile, epoxide, imine, enone, ketone, ester, allyl and benzyl groups within the organo radical. The reagent can be controlled so that it will selectively add to an organic electrophile such as an acid halide or aldehyde while other less reactive electrophilic groups are present. The reagent will also add under controlled conditions to epoxide, enone, imine and ketone groups.

11 Claims, No Drawings

HIGHLY REACTIVE FORM OF COPPER AND REAGENTS THEREOF

The present invention was made with Government support under Contract No. GM35153 awarded by the National Institute of Health. The Government has certain rights in the invention.

The present application is a Continuation-In-Part of U.S. application Ser. No. 07/692,236, filed Apr. 26, 1991, now abandoned.

BACKGROUND OF THE INVENTION

Organocopper reagents are highly desirable reagents for organic synthesis. They often react stereoselectively. Furthermore, they do not possess the extreme nucleophilicity of reagents such as Grignard reagents. Consequently, they can be used to synthesize organic compounds that are highly functionalized.

The chemistry of allyl organocopper reagents is illustrative of these characteristics. Allyl organocopper reagents have received renewed interest with Lipshutz's development of higher order allylic cyanocuprates, which have been shown to be among the most reactive cuprates yet developed. See, for example, B. H. Lipshutz et al., *J. Org. Chem.*, 54, 4977 (1989); B. H. Lipshutz et al., *J. Am. Chem. Soc.*, 112, 4063 (1990); and B. H. Lipshutz et al., *J. Am. Chem. Soc.*, 112, 4404 (1990).

The synthetic routes for production of organocopper reagents generally involve metathesis reactions of organolithium or Grignard reagents. Accordingly, functionalized organic substrates cannot be tolerated. For example, the allyl organocopper reagent is obtained only by an indirect synthesis involving the transmetalation of allylic stannates with an alkylcopper reagent, which was previously formed from a transmetalation of an organolithium or Grignard reagent. The problem with direct synthesis from an inorganic copper agent and an organic halide has been that the inorganic copper agent has either caused homocoupling of the organic halides or has not undergone oxidative addition with the organic halide.

An organocopper reagent can be produced directly from a highly reactive form of zerovalent copper, which is obtained from the reduction of copper(I) iodide phosphine complexes with a solution of lithium naphthalenide in tetrahydrofuran under argon. See, for example, R. D. Rieke et al., *Tetrahedron*, 45, 443 (1989); and R. D. Rieke et al., *Synth. Commun.*, 20, 2711 (1990). The active copper produced by this method will undergo oxidative addition to primary bromides, vinyl iodides, vinyl bromides, as well as aryl iodides and bromides. The organic halides can contain a limited number of functional groups such as esters, nitriles, and chlorides. The resulting organocopper reagents undergo typical lower order and higher order cuprate additions with electrophiles. However, the presence of the phosphine by-product represents a severe complication for product purification.

Therefore, an object of the invention is to produce a zerovalent copper reagent which is more reactive than that obtained with the copper(I) iodide phosphine method. A further object is the development of a zerovalent copper reagent that is free of phosphines. Another object is the direct production of highly functionalized aryl and alkyl cuprates from the corresponding halides. Yet another object is the direct production of highly functionalized allyl cuprates from the corresponding halides and acetates. Still another object is the production of bis- and tris- organocopper reagents by direct synthesis from zerovalent copper metal and organic compounds having two or more halogens.

SUMMARY OF THE INVENTION

These and other objects are achieved by the present invention which is directed to a new zerovalent copper species, a new organocopper reagent, and synthetic reactions performed with this organocopper reagent.

The zerovalent copper species is composed of zerovalent copper metal atoms in mixture or combination with an alkali metal salt of a halide or cyanide or both, preferably both. The species is formed from the reduction of a complex of a copper salt and an alkali metal salt of a halide with a reducing agent having a reduction potential of at least about 100 mV more negative than that of copper(I), and preferably at least about 100 mV more negative than that of copper(II). The copper salt is a copper cyanide or halide selected from the group consisting of copper(I) cyanide, copper(I) halides, copper(II) cyanide, and copper(II) halides. Preferably, the copper salt is a copper cyanide. More preferably, the copper cyanide is a copper(I) cyanide. For preferred embodiments, the zerovalent copper species in mixture or combination with an alkali metal salt of a cyanide also contains an alkali metal salt of thienylide. The zerovalent copper species is isolatable, i.e., capable of being isolated from the reaction mixture, and it is suspendable in an ethereal, polyethereal or hydrocarbon solvent such as ethyl ether, tetrahydrofuran, glyme, diglyme, benzene and the like.

The organocopper reagent is a mixture or combination of an organic cuprate and an alkali metal salt of cyanide, a halide, or both. Preferably, the organocopper reagent is a mixture or combination of an organic cuprate, alkali metal salt of cyanide, and an alkali metal salt of a halide. In preferred embodiments, the organocopper reagent can include an alkali metal salt of cyanide and an alkali metal salt of thienylide. The organic cuprate is an aliphatic, aryl, arylalkyl, heterocyclic or polymeric mono- or poly- cuprate. The organic cuprate is formed by reaction of the copper of the zerovalent copper species with an aliphatic, aryl, arylalkyl, heterocyclic or polymeric compound having one or more stable anionic leaving groups, such as halide for example. The aliphatic, aryl, arylalkyl or polymeric group of this reagent may optionally be functionalized with such compatible groups as olefin, ester, ketone, enone, epoxide, amide, ether aldehyde, imine, nitrile, acetate, halide, and carbamate. In the context of this invention, the term "aliphatic" means a saturated or unsaturated linear, branched or cyclic hydrocarbon radical; the term "heterocyclic" means a mono or polynuclear cyclic radical containing carbons and one or more heteroatoms such as nitrogen, oxygen or sulfur or a combination thereof in the ring or rings, including but not limited to pyridine, pyrrole, indole, thiazole, pyrazine, guanine, cytosine, thymine, adenine, uredine, uracil, oxazole, pyrazole, hydantoin, piperazine, quinoline, xanthene, acidine; the term "aryl" means a mono or polynuclear aromatic hydrocarbon radical; the term "arylalkyl" means a linear, branched or cyclic alkyl hydrocarbon radical having a mono or polynuclear aromatic hydrocarbon or heterocyclic substituent; and the term "polymeric" means a polyolefin, polyester, polyurethane, polyamide, polycarbonate, or polyether.

The organocopper reagent is reactive with a wide variety of organic electrophiles containing groups such as carboxylic acid halides, aldehydes, ketones, epoxides, enones, allyl halides, and imines. This reactivity is selective so that some of these electrophilic groups are preferred over others. In particular, depending upon the control of thermal conditions and stoichiometry, the organocopper reagent will selectively react with a carboxylic acid halide group in the presence of the other foregoing electrophilic groups. This selection is obtained at a very low temperature. At moderately low temperatures, the organocopper reagent will also react with aldehyde groups in the presence of epoxide, enone, ketone and imine groups. At slightly higher temperatures, the organocopper reagent will react with epoxide, enone and imine groups. At moderate temperatures, the organocopper reagent will react with ketone groups. The organocopper reagent will not readily react with ethers, esters, olefins, or nitrile groups. Thus, the organocopper reagent provides a direct route to difficult-to-make functionalized compounds as well as to heretofore unavailable compounds.

In preferred embodiments: (1) the copper species is a combination of zerovalent copper metal atoms and lithium cyanide and lithium bromide or chloride; (2) the organocopper reagent is formed from the oxidative addition of an aliphatic chloride or acetate, preferably an allylic chloride or acetate; and (3) the organocopper reagent can be selectively coupled with an imine, epoxide, enone, ketone, aldehyde, allyl halide, or carboxylic acid halide. Product isolation has been greatly simplified by this new phosphine-free reagent.

DETAILED DESCRIPTION OF THE INVENTION

The present invention is based upon the discovery of a zerovalent copper metal species that displays surprising and unexpected reactivity toward aliphatic, aryl, heterocyclic, arylalkyl and polymeric mono- or poly-halides (hereinafter organic halides) and allyl acetates, for example. It is believed that the copper species is a cluster of zerovalent copper atoms associated in some manner with the alkali metal salts provided by: (a) the coordinate complexing agent for the copper salt starting material; and (b) the salt produced from the cation of the reducing agent and the anion of the copper salt starting material. The cluster-salt association is most likely a surface phenomenon and is believed to facilitate the oxidative transfer reaction between the copper species and the organic halides without substantial homocoupling and without indiscriminate reaction with other electrophilic functional groups.

Notwithstanding these theoretical considerations, the zerovalent copper species of this invention is highly dispersable and/or partially soluble in ethereal, polyethereal, and hydrocarbon solvents at low temperature. The zerovalent copper species is readily isolatable, i.e., capable of being isolated from the reaction mixture in which it is made in relatively high yields, preferably quantitative yields. Furthermore, the zerovalent copper species of this invention will react with organic halides, and allyl acetates, at low temperature to produce selectively reactive organic cuprates.

The Zerovalent Copper Species

The zerovalent copper species of the present invention is composed of formally zerovalent copper metal atoms as highly dispersed particles. It is believed that these highly dispersed particles are also partially soluble in ethereal, polyethereal, and hydrocarbon solvents. By "formally zerovalent" copper metal atoms it is meant that the formal oxidation state, or charge, of the copper metal atoms is equal to the group number (i.e., 1) minus the number of unshared electrons (i.e., 1) minus the number of bonds (i.e., 0). The zerovalent copper species is a mixture or combination of formally zerovalent copper metal atoms and an alkali metal salt of a halide or cyanide or both. Preferably, an alkali metal salt of cyanide is present, and more preferably an alkali metal salt of cyanide and an alkai metal salt of a halide are present. In preferred embodiments the mixture or combination may also include an alkali metal salt of a thienyl group. The mixture or combination is highly dispersible in ethereal, polyethereal, or hydrocarbon solvents.

The zerovalent copper species can be produced by reaction of a reducing agent with a starting material complex of copper cyanide or halide, preferably cyanide, and an alkali metal salt of a halide. In alternative embodiments, the zerovalent copper species can be produced by reaction of a reducing agent with a starting material complex of copper cyanide containing a thienylide, such as lithium 2-thienylcyanocuprate. The starting copper species may be a copper(I) or copper(II) salt of a cyanide or halide, preferably it is a copper(I) cyanide or halide. It is especially preferred that copper cyanide be present in the complex. The halide of the salt (and the copper halide when used) may be F, Cl, Br, I; preferably Cl or Br. The alkali metal of the salt may be Li, Na, K, Rb, Cs. Preferably, the alkali metal salt is Li, Na or K, and most preferably it is Li.

Generally, the reducing agent may be any reagent that has a reduction potential at least 100 mV more negative than that of copper(I), and preferably at least 100 mV more negative than that of copper(II) if a Cu(II) cyanide or halide is present in the complex being reduced. Any reducing agent having a reduction potential of +0.90 mV will satisfy this relation. Examples include alkali metals; alkaline earth metals; alkaline earth metal salts of aromatic anions or alkali metal salts of aromatic anions, such salts being, for instance, sodium naphthalenide, lithium naphthalenide, sodium biphenylide, lithium biphenylide, sodium anthracenylide, or lithium anthracenylide; alkali metal hydrides such as lithium aluminum hydride, sodium borohydride, sodium hydride; metal intercalated graphites; and alkali metals dissolved in glymes or ethers.

The process for reduction to produce the zerovalent copper species is conducted under conditions designed to prevent its reoxidation. Generally, these conditions include use of nonhydroxylic solvents and the exclusion of oxygen. Also, the conditions are controlled so as to promote the existence of the copper atoms as small clusters and to avoid their agglomeration into larger configurations. Preferably, these conditions include low temperatures of less that about −30° C., preferably less than about −60° C., an inert atmosphere, and an ether or polyether solvent such as diethyl ether, dimethyl ether, tetrahydrofuran and the like. The starting material complex is soluble or highly dispersible in the solvent at this low temperature. The reduction can as well be conducted in a hydrocarbon solvent with N,N,N',N'-tetramethyl-ethylenediamine (TMEDA) to solubilize or disperse the starting material complex and reducing agent.

Although the copper species can be maintained for a time under these conditions, it is also quite reactive. Consequently, it is preferably synthesized immediately before use.

The Organocopper Reagent

Generally, the organocopper reagent of this invention is a mixture or combination of an aliphatic, aryl, heterocyclic, arylalkyl or polymeric mono- or polycuprate (hereinafter organic cuprate) and alkali metal salts. The cuprate moiety and alkali metal salts are derived from the foregoing zerovalent copper species. It is believed that, as occurs in the precursor copper species, the cuprate moiety or moieties of the organic cuprate associate in some manner with the alkali metal salts present to form the organocopper reagent. It is further believed that this association is in part responsible for the novel and selective reactivity of the organocopper reagent of this invention.

The organocopper reagent is produced by reaction of the zerovalent copper species with an aliphatic, aryl, heterocyclic, arylalkyl or polymeric compound having one or more stable anionic leaving groups such as halide, alkylcarbonyloxy, tosylate, triflate, or phosphonium ammonium, preferably halide or alkylcarbonyloxy, and more preferably halide. The copper species undergoes an oxidative transfer with the anionic leaving group or groups to form the cuprate moiety. If more than one leaving group of the same kind is present, the copper species will generally react first with leaving groups bound to sp3 carbons, second with those bound to sp2 carbons. If multiple leaving groups are present, the zerovalent copper species will generally react with all leaving group sites in the foregoing order until the species is completely consumed. The reaction is generally conducted under conditions designed to preserve the integrity of the organocopper reagent, those conditions including, for example, the exclusion of water and oxygen. Preferably, the conditions also include low temperature such as less than about −30° C., and more preferably less than about −60° C.

Generally, the organic group of the organic cuprate may be any saturated, olefinically unsaturated or aromatic hydrocarbon or a heterocycle containing carbon, nitrogen, oxygen, sulfur or combinations thereof in the heteronucleus, or the functionalized derivatives thereof, or a polymer based upon ethylenyl, ester, amide, urethane, carbonate or ether units or the functionalized derivatives thereof. The molecular size may range from organic compounds and monomers, typically having from 1 to about 300 carbons, to polymeric compounds having molecular weights up to and including the million range. Preferred aliphatic, aryl, heterocyclic and arylalkyl groups include linear or branched alkyl, cycloalkyl, allyl, vinyl, phenyl, benzyl, pyridyl, quinolinyl, piperadinyl, cytosinyl, uracinyl, guaninyl, adenosinyl, pyrrolyl, thiazolyl, the methylenyl derivatives of such heterocycles and phenyl alkyl groups as well as the hydrocarbon substituted and/or functionalized forms thereof. The hydrocarbon substituents may be one or more of such groups as alkyl, cycloalkyl, heterocyclic, olefinic and aromatic groups as well as combinations thereof, each substituent having from 1 to about 30 carbons. The substituent or substituents are bound to aliphatic, aromatic or arylalkyl groups such that they do not sterically hinder access to the leaving group. The functional group or groups may be bound to the aliphatic, aromatic or arylalkyl group and/or to the hydrocarbon substituents thereof and include such functional groups as olefin, ester, ketone, enone, epoxide, ether, amide, aldehyde, imine, halide, acetate, carbamate, and nitrile.

Generally, the organocopper reagent will selectively react first with carboxylic acid halide groups at very low temperatures such as less than about −60° C. and under stoichiometric conditions. This reaction will selectively occur in the presence of olefin, aldehyde, ketone, enone, epoxide, imine, ether, nitrile, amide, and ester groups. Under stoichiometric conditions at moderately low temperatures within a range of from about −50° C. to −30° C. and without the presence of acid halide groups, the organocopper reagent will selectively react with aldehyde groups in the presence of ketone, enone, epoxide, imine, nitrile, ether and ester groups. At slightly higher temperatures such as no less than about −20° C., the organocopper reagent will react with enone, imine and epoxide groups in the presence of ketone, ether, nitrile and ester groups. At moderate temperatures within a range no less than about 0° C., the organocopper will react with ketone groups in the presence of nitrile, ether or ester groups. The organocopper reagent will also react with readily displacible organic halides at moderate temperatures. It will not, however, readily react with vinyl, ester, ether, or nitrile groups.

Although the organocopper reagent may be functionalized as outlined above, it will maintain a stable state and will not self-react as long as it is maintained within the appropriate low temperature range. It is believed that the presence of the alkali metal salts, which combine with the organic cuprate in some manner to form the organocopper reagent of this invention, contribute to this stability and selectivity. In such instances, the electrophile to be added to the organocopper reagent will have a higher affinity for the cuprate portion than does the functional moiety contained within the organic group.

Generally, the coupling reaction between the organocopper reagent and the organic electrophile is conducted in the same medium used to produce the organocopper reagent. The reaction is conducted under conditions designed to favor the production of the desired coupled product. Those conditions generally include low temperature, use of appropriate electrophiles as indicated above, addition of the electrophile to the organocopper reagent and stirring with appropriate reaction times. One or more of these conditions will be appropriate for use in particular instances. Choice of some or all of them is within the ordinary artisan's skill.

The reagents and reactions of this invention are useful in the organic synthesis of organic compounds that are difficult or impossible to prepare by other techniques. In particular, the facility to directly couple aliphatic, aryl and arylalkyl groups to organic acid halides, aldehydes or imines in the presence of other functional groups such as esters, ketones, enones, epoxides, amides, allyls and nitriles under controlled conditions enables great latitude in synthetic design. Moreover, the organocopper reagent of this invention will undergo a heretofore unknown addition to enones and epoxides. It is indeed a highly novel and unexpected discovery that allyl and similar groups can be directly coupled to acid halides and the like without the use of intermediate organolithium or Grignard compounds or phosphines. This characteristic permits the presence of many functional groups which would otherwise react with intermediate organolithium or Grignard compounds. This facility promotes the use of the reagents and reactions of this invention in the organic synthesis of highly functional pharmaceutical compounds, insecticides, herbicides, polymeric compounds, organic additives for polymer compositions, organic conductors, and organic information storage devices. Specific examples include the syntheses of prostaglandins, penicillins, tranquilizers and carbocylic anticancer agents. These syntheses are made more efficient, are economically feasible, do not involve difficult separation problems owing to the absence of phosphines. They open the synthetic and investigatory arenas to the development and use of rare or unavailable organic compounds.

PREFERRED EMBODIMENTS

The CuCN.2LiBr-Based Copper Species

A preferred embodiment of the copper species is formed from a complex of copper(I) cyanide and a lithium halide. Specifically, the CuCN.2LiBr or CuCN.2LiCl complex can be reduced at low temperature such as about −100° or −110° C. to produce a zerovalent copper species that reacts with aliphatic, aryl and arylalkyl iodides, bromides, and chlorides as well as aliphatic acetates, preferably, allylic halides or acetates. The product is an organocopper reagent containing alkali metal salts of cyanide and halides.

The Thienyl-Based Copper Species

Another preferred embodiment of the copper species is formed from a complex of copper(I) cyanide containing a thienylide. Specifically, the alkali metal salts of thienylcyanocuprates, such as lithium 2-thienylcyanocuprate, can be reduced at low temperatures, such as about −78° or below, preferably between about −78° C. and −110° C., to produce a zerovalent copper species that reacts with aliphatic, aryl and arylalkyl iodides, bromides, and chlorides as well as aliphatic acetates, preferably, allylic halides or acetates. The product is an organocopper reagent containing alkali metal salts of cyanide and thienylide.

The advantages of the zerovalent copper species of the present invention are in their use in the production of useful, and preferably highly functionalized, organocopper reagents in high yields. Certain advantage results from the fact that very little homocoupling of the organic halide is seen in the products of the reactions between the organic halides and the zerovalent copper species. For example, generally and preferably less than about 5% homocoupling, often less than about 1% homocoupling, is typically observed by gas chromatography. Other advantage results from the fact that eliminated by-products such as alkene are generally seen for the alkyl halides in very low yield, i.e., only about 5–10% yield. Thus, formation of functionalized organocopper reagents containing chloride, nitrile, and ester functionalities can be conveniently produced from the zerovalent copper species of the present invention.

The Organocopper Reagent

Significantly, the zerovalent copper species of the present invention reacts with alkyl, allylic, vinyl or phenyl halides and acetates at low temperature, such as −100° C., preferably −70° C., to produce the corresponding alkyl, allylic, vinyl, pyridyl, 2-methylenylpyridyl or phenyl organocopper reagent with less than 10% of the homocoupled by-product.

To demonstrate the reactivity and character of this embodiment, examples of the functionalized alkyl organocopper reagents can be trapped with benzoyl chloride to produce the ketones shown in Table I of Example 2. These examples of organocopper reagents can also be reacted in high yield with enones to produce the 1,4 addition products as shown in Table II of Example 3. In another example, non-functionalized allyl organocopper reagents react in high yield with benzoyl chloride to produce the beta,gamma-unsaturated ketones as shown in Table III of Example 4. These non-functionalized allyl organocopper reagents will also react with a variety of other electrophiles, including benzaldehyde, cyclohexenone, and electrophiles containing epoxide and nitrile functionality, as shown in Table III of Example 4. Further examples of the reactivity of allyl chlorides and acetates with the thienyl-based zerovalent copper species are shown in Tables XI–XIII of Example 8.

The invention allows for the formation of unique functionalized allyl organocopper reagents by reaction of the active copper species with allyl chlorides containing a diverse range of functionality as shown in Table IV of Example 5. Significantly, the use of MeLi (methyl lithium) in these reactions improves the nucleophilicity of the allylic organocopper reagents, whether functionalized or not, such that they undergo substitutions with epoxides, as shown in Table III of Example 4. In these reactions, about 0.5–1.0 equivalent of MeLi is used relative to the amount of organocopper reagent. Interestingly, the addition of MeLi to an allylcopper chloride containing an epoxide group resulted in intramolecular opening of the epoxide producing a bicyclic product, as discussed in Example 5.

The active copper species can further be utilized in the formation of bis-organocopper complexes containing a variety of hybridized carbons. Subsequent reactivity can be controlled as shown in Scheme 1 of Example 6, and Table VI of Example 7. Further illustrations of the novel bis and propargyl organocopper reagents according to the invention are presented in Table V following Example 6. Intramolecular coupling can also be accomplished under appropriate controlled temperature conditions. Illustrations of such intramolecular coupling is shown in Table VII. Table VIII illustrates a new class of acyl cuprate formed by reaction of a carboxylic acid halide with the zerovalent copper species according to the invention. Table IX illustrates a new reaction for deoxygenation of sulfoxides, sulfones, and sulfonates with the zerovalent copper species according to the invention. Table X illustrates examples of heterocyclic organocopper reagents made according to the invention.

Preferred embodiments for the industrial use of the organocopper reagents of this invention are based upon the pharmaceutical arts. For example, the vinyl organocopper reagent shown below can be used in a short synthetic approach to prostanoids which are well-known pharmaceutical compounds, see The Merck Index, 10th Ed., Merck & Co. Pub. 1983, pg. 7778.

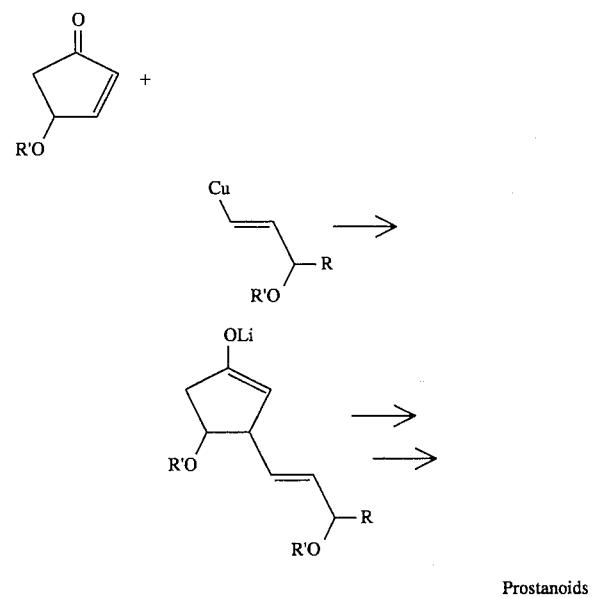

Prostanoids

Intramolecular addition to alkynes also can provide pharmaceutical and insect behavior modification compounds. Since the organocuprates formed from oxidative addition of the active copper species to organohalides can tolerate significant functionality, acetylenes can be incorporated into the organohalides used. This incorporation would allow for the intramolecular addition of an organocuprate to an acetylene. This previously unknown reaction provides a convenient way to construct a large variety of carbocycles and heterocycles. Some reactions envisioned result in the synthesis of exomethylene compounds (equation 6), indenes, benzofurans and indoles (equation 7) and a variety of other compounds.

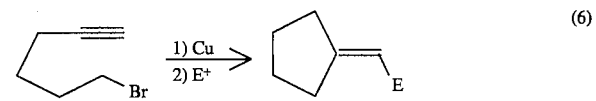
(6)

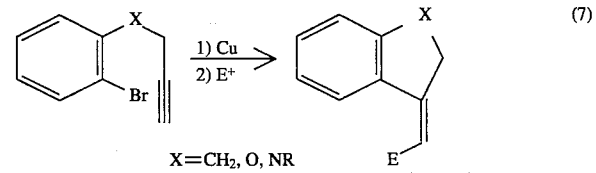
(7)

X=CH₂, O, NR

Some simple natural products are also accessible using this methodology (equations 8 and 9).

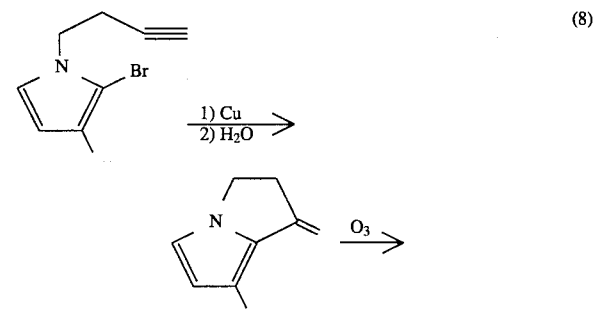
(8)

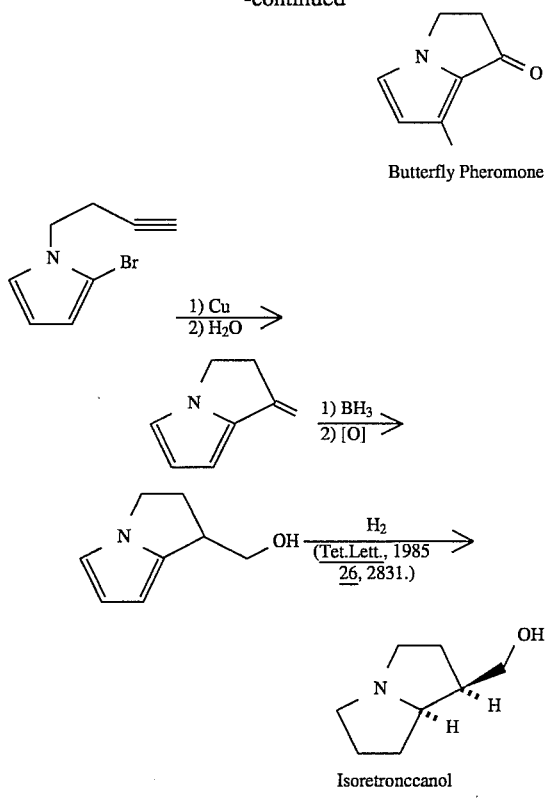

Butterfly Pheromone (9)

Isoretronccanol

Conjugate addition followed by nucleophilic ring closure also provides natural products. The alkylcopper species derived from the copper species is very reactive in conjugate addition reactions with 2-cyclohexenone, giving the 3-alkylated cyclohexanones in generally good to excellent yields. A specific example is shown below. The resulting enolate anion undergoes an addition-elimination cyclization if allowed to.

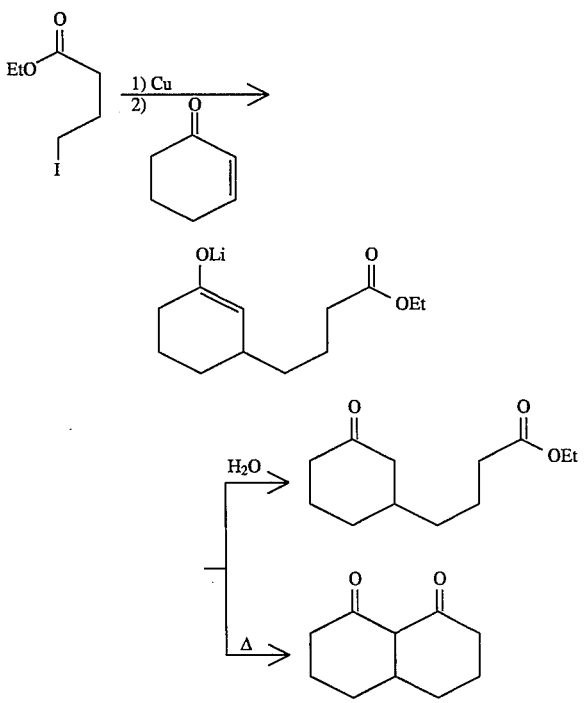

This approach offers the possibility of forming a variety of bicyclic organic systems useful in pharmaceutical arts.

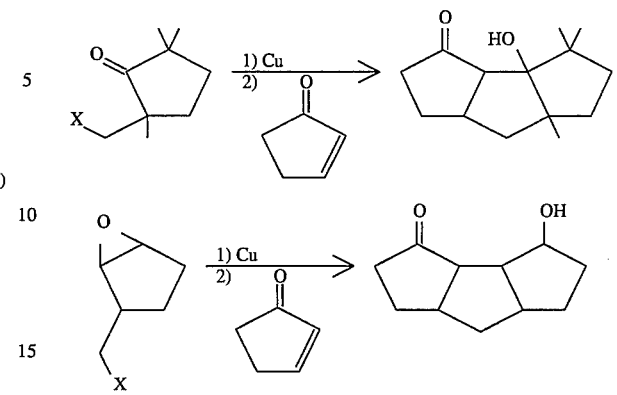

One such important ring skeleton is the above-depicted 5-5-5 tricyclic structure. Most naturally occurring condensed tricyclopentanoids are tricyclic sesquiterpenes. Hirsutene, coriolin, hirsutic acid, and capnellene have a linearly-fused tricyclopentane structure. These compounds come from a wide variety of natural sources and many possess significant biological activity such as anticancer activity. In the past two decades, there has been intense activity in the development of synthetic routes to these compounds. The reactions of the organocopper reagents of this invention offer a new, elegant, and effective synthetic approach to these naturally occurring triquinanes.

The invention will be further exemplified with respect to the various specific and preferred embodiments and techniques. It should be understood, however, that many variations and modifications may be made while remaining within the scope of the invention.

EXPERIMENTAL EXAMPLES

All manipulations were carried out in Schlenk apparatus, connected to a dual manifold providing vacuum and argon. The Linde™ prepurified grade argon was further purified with a BASF R3-11 catalyst column at 150° C., a phosphorus pentoxide column, and a column of granular potassium hydroxide. Lithium, naphthalene, CuCN, LiCl and LiBr were weighed as needed in an argon Vacuum Atmosphere Co. drybox. All chemicals were purchased from Aldrich Chemical Co. and used without further purification unless otherwise specified. LiCl and LiBr were dried at 120° C., 0.5 torr, overnight before being transferred to the drybox. Tetrahydrofuran (THF) was distilled from Na/K alloy under an argon atmosphere immediately before use. Low temperature conditions were maintained by utilizing a Neslab endocal ULT-80 refrigerated circulating bath or by utilizing dry ice/acetone baths.

NMR spectra were obtained from a Nicolet NT-360, Varian VXR-200, G.E. Omega-500 or G.E. Omega-300. All NMR samples were dissolved in $CDCl_3$. $^1H$ NMR spectra chemical shifts are reported in parts per million ($\delta$) downfield from trimethylsilyl chloride (TMSCl) as an internal standard. $^{13}C$ NMR chemical shifts ($\delta$) were reported in reference to the 77.00 ppm peak for $CDCl_3$. Infrared spectra were recorded on a Perkin-Elmer 283 IR spectrophotometer. Analytical GC was performed on a Hewlett-Packard 5890A gas chromatograph equipped with 12 ft lengths of ⅛ inch stainless steel tubing packed with 5% SP 2100 or SP 2250 on a Supelco support, and interfaced with a Perkin-Elmer LCI-100 integrator. GC yields were quantified by determining response factors for pure samples and calculating the yield relative to an internal standard.

Product purification was typically performed by column chromatography with use of Merck flash silica gel 60 (230–400 mesh). Fractions were monitored with analytical thin-layer aluminum-backed Merck 5735 indicating plates precoated with silica gel 60 $F_{254}$ (layer thickness 0.2 mm). If the product was not UV active, the thin-layer plates were typically developed with a vanillin solution. Elemental analyses were performed by Galbraith Labs, Knoxville, Tenn. High resolution mass spectra were obtained from the Midwest Regional Center of Mass Spectrometry, University of Nebraska-Lincoln.

EXAMPLE 1

Preparation of Zerovalent Copper Species

Method A

Lithium (8.46 mmol) and naphthalene (10.1 mmol) were combined with anhydrous tetrahydrofuran (THF) (15 ml) and stirred under argon until the Li was consumed (approximately 2 h). The flask was then cooled to $-100°$ C. CuCN (8.00 mmol) and LiBr (17.27 mmol) in THF (5 ml) were stirred under argon until the Cu(I) salt was solubilized. The CuCN.2LiBr solution was cooled to $-40°$ C. and transferred into the lithium naphthalide (LiNp) with a cannula. The solution was stirred for 5 min. The resulting zerovalent copper species was, i.e., active copper, was ready for immediate use.

Method B

Lithium (14.0 mmol) and naphthalene (15.1 mmol) were placed in a 100 ml round-bottomed flask in an argon dry box and sealed with a septa. In the same argon dry box, CuCN (12.0 mmol) and LiCl (23.1 mmol) were placed in a 50 ml round-bottomed flask and sealed with a septa. The two round-bottomed flasks were connected to a dual manifold vacuum-argon line. All steps were conducted under a positive pressure of argon. Dry THF (20 ml) was added to the flask containing the Li and naphthalene and the dark green solution was allowed to stir for 2½ hours. During this time, 12 ml of dry THF was added to the flask containing the CuCN and LiCl. The solution turned a pale yellow. The LiNp solution was then cooled to $-100°$ C. (4:1 hexane, $Et_2O$ mixture in liquid $N_2$) and the CuCN.2LiCl was cooled to $0°$ C. The CuCN.2LiCl was transferred via cannula to the LiNp solution at $-100°$ C. and stirred for 10 minutes. The resulting zerovalent copper species, i.e., active copper, was ready for immediate use.

Method C

Lithium metal (8.40 mmol) and naphthalene (9.20 mmol) in freshly distilled THF (10 ml) were stirred at room temperature under an argon atmosphere for two hours, and then cooled to $-108°$ C. To this dark green preformed lithium naphthalenide solution was added a cold solution, $-50°$ C., of lithium 2-thienylcyanocuprate (0.25M, 32 ml, 8.00 mmol) via cannula. The dark black-brown solution of active copper was used after stirring at $-108°$ C. for 10–30 minutes.

EXAMPLE 2

Functionalized organocopper reagents were prepared from organic halides and the zerovalent copper species prepared according to the procedure of Method A of Example 1. These organocopper reagents can be cross-coupled with benzoyl chloride at $-35°$ C. in 30 minutes to produce functionalized ketones in good to excellent yields (Table I).

A representative procedure for the formation of a functionalized ketone is as follows. The active copper species from Example 1 in THF was warmed to $-35°$ C. and charged with ethyl 4-bromobutyrate (1.95 mmol). The solution was stirred for 10 min. (For aryl halides, the solution was warmed to $0°$ C., immediately charged with aryl halide, and allowed to mix for 1 h.) The resultant organocopper reagent was ready for use in acid chloride coupling reactions or conjugate addition reactions. To the organocopper reagent was added benzoyl chloride (3 equiv based on the amount of organocopper reagent used) neat via syringe at $-35°$ C. The solution was stirred for 30 min, quenched with $NH_4Cl$ (satd, 5 ml), and isolated with standard flash silica gel chromatographic techniques.

TABLE I

Cross-Coupling of Benzoyl Chloride with Organocopper Reagents Derived from CuCN.2LiBr-Based Copper

| entry | halide (equiv)[a] | product[b] | % yield[c] |
|---|---|---|---|
| 1 | $Br(CH_2)_7CH_3$(0.25) | $PhCO(CH_2)_7CH$ | 82 |
| 2 | $Br(CH_2)_6Cl$(0.25) | $PhCO(CH_2)_6Cl^3$ | 80 |
| 3 | $Br(CH_2)_3CO_2Et$(0.25) | $PhCO(CH_2)_3CO_2Et$ | 81 |
| 4 | $Br(CH_2)_2CO_2Et$(0.25) | $PhCO(CH_2)_2CO_2Et$ | 43 |
| 5 | $Br(CH_2)_3CN$(0.25) | $PhCO(CH_2)_3CN$ | 86 |
| 6 | bromobenzene(0.20) | PhCOPh | 87 |
| 7 | $p-BrC_6H_4CN$(0.20) | $p-NCC_6H_4COPh$ | 60 |
| 8 | $o-BrC_6H_4CN$(0.20) | $o-NCC_6H_4COPh$ | 74 |
| 9 | $o-BrC_6H_4CO_2Et$(0.20) | $EtO_2CC_6H_4COPh$ | 51 |
| 10 | $p-BrC_6H_4Cl$(0.20) | $p-ClC_6H_4COPh$ | 83 |

[a]Based on 1 equiv of CuCN, alkyl halides were allowed to react for 10 min at $-35°$ C. Aryl halides were added at $0°$ C. and allowed to react for 1 h.
[b]All products gave consistent $^1H$ and $^{13}C$ NMR spectra.
[c]Isolated yields.

The products were easily isolated via flash silica gel chromatography. An excess of acid chloride is generally used (generally 2–3 equiv based on the amount of organocopper reagent) because unreacted active copper will react with acid chlorides.

EXAMPLE 3

The organocopper reagents of the invention can also be added to enones as indicated in Table II. The addition of trimethylsilyl chloride (TMSCl) (see, for example, E. J. Corey et al., *Tetrahedron Lett.*, 26, 6015 (1985); E. J. Corey et al., *Tetrahedron Lett.*, 26, 6019 (1985); and A. Alexakis et al., *Tetrahedron Lett.*, 27, 1047 (1986)) to the organocopper reagents made from CuCN.2LiBr-based active copper, i.e., the preferred zerovalent copper species of the present invention, and the halides listed in Table II allowed for 1,4-conjugate additions to occur readily at $-78°$ C. in good to excellent yields (Table II).

The halide, 0.25–0.30 equiv based on 1 equiv of CuCN, was transferred to the active copper species in THF at $-35°$ C. After 15 min, the flask was cooled to $-78°$ C. A 2- to 3-fold excess of TMSCl, relative to the amount of the 1,4-adduct used, was injected neat into the flask (a 6-fold excess of TMSCl was used for Entry 6 in Table II). The 1,4-adduct, i.e., enone, was dissolved in THF (10 ml) in a separate vial and delivered dropwise with stirring to the organocopper solution. After 1.5 h at $-78°$ C., the flask was gradually warmed to room temperature.

TABLE II

Conjugate Additions with Organocopper
Reagents Derived from CuCN.2LiBr-Based Active Copper

| entry | halide | enone[a] (equiv) | % yield[b] |
|---|---|---|---|
| 1 | $Br(CH_2)_7CH_3$ | A (0.17) | 92 |
| 2 | $Cl(CH_2)_7CH_3$ | A (0.16) | 42 |
| 3 | $Br(CH_2)_3CO_2Et$ | A (0.17) | 70 |
| 4 | $Br(CH_2)_3CO_2Et$ | A (0.12) | 90 |
| 5 | $Br(CH_2)_3CO_2Et$ | B (0.11) | 94 |
| 6 | $Br(CH_2)_3CO_2Et$ | C (0.11) | 87 |
| 7 | $Br(CH_2)_3CN$ | A (0.12) | 87 |
| 8 | $Br(CH_2)_3CN$ | B (0.11) | 92 |
| 9 | $Br(CH_2)_6Cl$ | A (0.12) | 82 |
| 10 | $BrC_6H_{11}$ | A (0.12) | 80 |
| 11 | $BrC_6H_5$ | A (0.11) | 45 |
| 12 | $ClCH_2CH=C(CH_3)_2$ | A (0.10) | 81[c] |

[a]Enone: A = 2-cyclohexen-1-one, B = 4-hexen-3-one. C = trans-cinnamaldehyde. The number of equivalents of the enone was based on the amount of CuCN used in the preparation of the zerovalent copper species.
[b]Isolated yield of 1,4-conjugate addition product (not shown). All products gave consistent IR, HRMS, and $^1H$ and $^{13}C$ NMR spectra.
[c]The enone was injected neat at −90° C. 3-(3-Methyl-2-butenyl)cyclohexanone was the sole product isolated.

Both cyclic and acyclic enones can be used in these 1,4-conjugate addition reactions. Generally, the ideal organocopper reagent to enone ratio is approximately 2.5:1, i.e., 2.5 moles of organocopper reagent to 1 mole of eneone. These functionalized organocopper reagents also add to α,β-unsaturated aldehydes in the presence of TMSCl to afford highly functionalized aldehydes (see Entry 6 in Table II). The competitive 1,2-addition was not seen by GC analysis.

EXAMPLE 4

The active zerovalent copper species of the present invention reacts with allylic chlorides or acetates to form the corresponding allyl, i.e., allylic, organocopper reagents. The resulting organocopper reagents were cross-coupled with various electrophiles, such as benzoyl chloride, to produce the products shown in Table III.

Unsymmetrical allyl chlorides presumably yield the primary organocopper reagent upon reaction with active copper. Since the 1,4-conjugate addition of prenylcopper with cyclohexanone proceeded via α attack (Table II, Entry 12), reaction of prenylcopper with benzoyl chloride must involve γ attack (Table III, Entry 7).

The reaction of allyl acetates is somewhat more limited than analogous reactions of allyl chlorides. This is because disubstitution in either the alpha or gamma positions render them less reactive towards the zerovalent copper or the present invention (yield of Entry 6 in Table III only 27%). The reaction of crotyl acetate with benzaldehyde produced a 70:30 syn to anti mixture of the resulting homoally alcohol (Entry 5, Table III).

Addition of ketones was also carried out (Table III, Entries 11 and 12) with chemoselective reaction to the carbonyl in the presence of nitrile functionality (Entry 13). Thus, the formation of homoallyl alcohols containing nitrile groups is possible from the appropriate ketone or aldehyde.

The addition of MeLi increased the nucleophilicity of these allylic organocopper reagents such that they underwent substitution with epoxides (Table III, Entry 10). Without the addition of MeLi only 6% of the alcohol product was seen. Upon addition of MeLi, the yield increased to 67%.

TABLE III

Reaction of Non-Functionalized Allyl
Chloride and Acetates with Zerovalent Active Copper
and Cross-Coupling with Various Electrophiles

| Entry | RX[a] | E[+] | Product | Isolated Yield[b,c] |
|---|---|---|---|---|
| 1 | allyl-Cl | PhCOCl | PhC(O)CH₂CH=CH₂ | 65% |
| 2 | allyl-OAc | PhCOCl | PhC(O)CH₂CH=CH₂ | 63% |
| 3 | methallyl-Cl | PhCOCl | PhC(O)CH₂C(CH₃)=CH₂ | 75% |

TABLE III-continued

Reaction of Non-Functionalized Allyl
Chloride and Acetates with Zerovalent Active Copper
and Cross-Coupling with Various Electrophiles

| Entry | RX[a] | E[+] | Product | Isolated Yield[b,c] |
|---|---|---|---|---|
| 4 | CH₂=C(CH₃)CH₂OAc | PhCHO | Ph-CH(OH)-CH₂-C(CH₃)=CH₂ | 79% |
| 5 | CH₃CH=CHCH₂OAc[d] | PhCHO | Ph-CH(OH)-CH(CH₃)-CH=CH₂ [e] | 81% |
| 6 | (CH₃)₂C=CHCH₂OAc | PhCHO | Ph-CH(OH)-C(CH₃)₂-CH=CH₂ | 27% |
| 7 | (CH₃)₂C=CHCH₂Cl | PhCOCl | Ph-CO-C(CH₃)₂-CH=CH₂ | 74% |
| 8 | CH₂=CH-CH(Cl)CH₃ | PhCOCl | Ph-CO-CH(CH₃)-CH=CH₂ | 72% |
| 9 | (CH₃)₂C=CHCH₂Cl | cyclohexenone[f] | 3-(3-methyl-2-butenyl)cyclohexanone | 81% |
| 10 | CH₂=C(CH₃)CH₂Cl | epoxide[g] | CH₂=C(CH₃)-CH₂-CH(OH)-(CH₂)₃CH₃ | 67% |
| 11 | CH₂=C(CH₃)CH₂Cl | PhCOCH₃ | Ph-C(OH)(CH₃)-CH₂-C(CH₃)=CH₂ | 91% |
| 12 | CH₂=C(CH₃)CH₂Cl | O=C(CH₃)-(CH₂)₂-C≡N | (CH₃)(OH)C(CH₂C(CH₃)=CH₂)-(CH₂)₂-C≡N | 77% |

[a]The ratio between allyl chloride and the active copper was 0.4 to 1 (the number of moles of active copper being equal to the number of moles of the CuCN starting material). The ratio between allyl acetate and the active copper was 0.25 to 1 (the number of moles of active copper being equal to the number of moles of the CuCN starting material).
[b]Isolated yields.
[c]For reactions with PhCOCl as the electrophile, the yields were based on RCl or ROAc as the limiting reagent because a 3-fold excess of the acid chloride was used (based on the number of moles of RCl or ROAc). For reactions using all other electrophiles, the yields were based on the electrophile as the limiting reagent because the molar ratio of RCl or ROAc used to electrophile was about 2.0:1 to 2.5:1.
[d]98% trans isomer.
[e]A 70:30 mixture of syn and anti diastereoisomers was observed by NMR.
[f]A three-fold excess of TMSCl relative to the amount of cyclohexenone was added prior to enone addition.
[g]Two equivalents of MeLi relative to the amount of RCl was added to the mixture prior to the addition of the epoxide.

Typical Procedure for the Formation of Allyl Organocopper Reagents and Cross-Coupling with Acid Chlorides To a solution of active copper at −100° C. was added the allyl chloride or acetate (0.25 equiv relative to the copper as CuCN) to avoid Wurtz-type by-products. To further diminish homocoupling, the allyl chlorides were cooled to −78° C. in a vial admixed with THF (1 ml) prior to the addition to the active copper. If the mixture was at about −100° C., it was allowed to warm to −78° C. and maintained at that temperature for about 10 min. The oxidative additions between the copper and the allyl chlorides or acetates typically were complete in less than about 5 min. VPC analysis showed that less than 10% of homocoupled by-product was formed. The electrophile was added to the allyl organocopper at −90° C. to −100° C. and allowed to warm typically to −20° C. For example, PhCOCl (3 equiv based on the amount of organocopper reagent present) was added neat via syringe at −100° C. and allowed to react for 15 min. After work-up, the products were easily isolated via flash silica gel chromatography.

5-Hydroxy-5,7-dimethyl-7-octenonitrile (Entry 12, Table III)

$R_f$=0.11 in 4:1 (v/v) hexane and ethyl acetate, respectively (77% yield): IR (neat) 3477, 3074, 2970, 2929, 2247, 1714, 1643, 1458, 1427, 1375, 1319, 1236, 1151, 1109, 929, 893, 787 $cm^{-1}$. $^1H$ NMR (360 MHz) 4.97–4.91 (m, 1H), 4.79–4.72 (m, 1H), 2.38 (t, J=6.9 Hz, 2H), 2.25– 2.15 (m, 2H), 1.85–1.83 (m, 3H), 1.82–1.74 (m, 2H), 1.62– 1.57 (m, 2H), 1.19 (s, 3H). $^{13}C$ NMR (50 MHz) 142.1, 119.6, 115.1, 71.7, 49.6, 40.9, 26.8, 24.9, 20.1, 17.4.

Typical Procedure for Intermolecular Epoxide Openings

Methallylchloride (3.16 mmol) was weighed into an 8 ml vial, sealed with a septum and placed under argon. THF (2 to 4 ml) was added to the vial and the allyl chloride solution was cooled to −78° C. The allyl chloride was added rapidly via a cannula to a suspension of the zerovalent copper species prepared according to the procedure of Example 1 (7.96 mmol) at −100° C. and stirred for 10 min. MeLi (6.30 mmol) was added to the newly formed organocopper solution at −90° C. and stirred for 15 min. 1,2-Epoxyhexane (1.01 mmol) was added from a vial to the new organocopper solution at −90° C., warmed to 0° C. over 3 hours, and held at 0° C. for 12 hours. The reaction was quenched with $NH_4Cl$ (sat'd), extracted with $Et_2O$ (2×50 ml), washed with brine (2×50 ml), and dried over $MgSO_4$. Flash silica gel chromatography, using gradient mixtures of hexane and ethyl acetate, afforded 2-methyl-1-nonen-5-ol (0.68 mmol, Entry 10 in Table III). $R_f$=0.23 in 9:1 (v/v) hexane and ethyl acetate, respectively (67% yield): IR (neat) 3317, 3070, 3016, 2954, 2931, 2869, 2854, 1647, 1452, 1375, 1126, 1084, 1053, 1036, 1003, 885 $cm^{-1}$. $^1H$ NMR (360 MHz) 4.72 (bs, 2H), 3.63–3.58 (m, 1H), 2.20–2.05 (m, 2H), 1.74 (s, 3H), 1.68–1.30 (m, 8H), 0.91 (t, J=7.0 Hz, 3H). $^{13}C$ NMR (50 MHz) 145.9, 110.0, 71.7, 37.2, 35.2, 34.0, 27.8, 22.7, 22.4, 14.0.

Procedure for the Conjugate Addition of a Cyclic Allyl Organocopper Reagent

In an effort to diminish homocoupling, 3-chlorocyclohexene (3.20 mmol) was weighed in a large vial and capped with a septum. Once under an argon atmosphere, THF (10 ml) was added to the vial. To a stirring active copper solution (8.23 mmol in 23 ml of THF) at −95° C., the allyl chloride is delivered dropwise from a cannula, over 30 minutes. After 5 minutes, TMSCl (2.84 mmol) is injected neat prior to the neat, dropwise injection of 2-cyclohexenone (0.82 mmol). The reaction flask is placed in a −78° C. bath and allowed to gradually warm to room temperature. The reaction mixture is quenched with $NH_4Cl$ (sat'd) (50 ml) and $Et_2O$ (25 ml) is added prior to further extraction of the organic layer with 0.5M HCl (50 ml), water (50 ml), and brine (50 ml). The combined aqueous layers are back extracted with $Et_2O$ (30 ml). The combined organic layers are dried with $MgSO_4$ and reduced in volume for column chromatography. 3-(2-cyclohexenyl)cyclohexanone (0.43 mmol) was isolated in 52% yield (not shown in Table III). $R_f$=0.31 in 9:1 (v/v) hexane and ethyl acetate, respectively. $^1H$ NMR (300 MHz) 5.73–5.67 (m, 1H), 5.53–5.50 (m, 1H), 2.37–1.16 (m, 16H). $^{13}C$ NMR (75 MHz) 212.50, 212.47, 129.1, 128.8, 128.7, 128.5, 45.2, 45.0, 43.6, 41.4, 40.0, 39.9, 28.4, 28.1, 25.52, 25.46, 25.41, 25.3, 25.2, 25.1, 21.8, 21.7.

EXAMPLE 5

The reaction of the zerovalent active copper species of the present invention with functionalized allylic chlorides produced the first known, preformed functionalized allylic organocopper reagents. These functionalized allylic organocopper reagents can contain ketone, alpha,beta-unsaturated ketone, ester, epoxide, alkyl acetate, alkyl chloride, carbamate, and nitrile functionalities. The resulting functionalized allylic organocopper reagents react with a variety of electrophiles to produce highly functionalized organic products, as shown in Table IV.

In a typical procedure, the functionalized allyl chloride (0.4 equiv relative to the number of moles of CuCN used to prepare the zerovalent copper species) was combined with 4 ml of THF and cooled to −78° C. This solution was then added to the active copper suspension at −100° C. and allowed to stir for 10 min. The electrophile (0.2 equiv based on the amount of the organocopper reagent) was combined with 2 ml of THF, and added to the functionalized allylic organocopper reagents at −90° C. The solution was allowed to warm to −20° C. over the course of two to three hours.

The functionalized allylic organocopper reagents derived from primary allyl chlorides show remarkable thermostability with little decomposition even at 0° C. (Table IV, Entries 1 and 4). The functionalized allylic organocopper reagents made from secondary allyl chlorides decomposed at a significant rate (within one hour) at 0° C. Thus, for these reagents, the subsequent addition of the electrophile was conducted almost immediately to their formation.

Like the allyl organocopper reagents containing no functionality (Table III, Entry 5), the functionalized allyllic organocopper reagents whose functional group is distant from the carbon-copper bond show limited diasteroselectivity. However, the presence of a carbonyl group two carbons from the gamma position increases the syn isomer above 97% (Table IV, Entry 3).

As stated above, the addition of MeLi to the allyl organocopper species increases the reactivity of the allyl organocopper reagent such that reactions with epoxides occur (Table III, Entry 10). When MeLi was added to the functionalized organocopper species derived from the zerovalent copper of the present invention and an allyl chloride containing an epoxide group, an intramolecular opening of the epoxide produced a bicyclic product (Table IV, Entry 17).

See Scheme 1. Thus, the zerovalent copper species of the present invention can be used to prepare an intramolecular cyclization of an organocuprate reagent. This method involves contacting an organic compound having one or more stable anionic leaving groups and an electrophilic functionality with a first combination of zerovalent copper metal atoms and an alkali metal salt to produce a second combination of an organic mono- or poly- cyclic cuprate and the alkali metal salt, wherein the alkali metal salt has an anion of halide or cyanide or both. This method is preferably assisted by the addition of MeLi.

Scheme 1

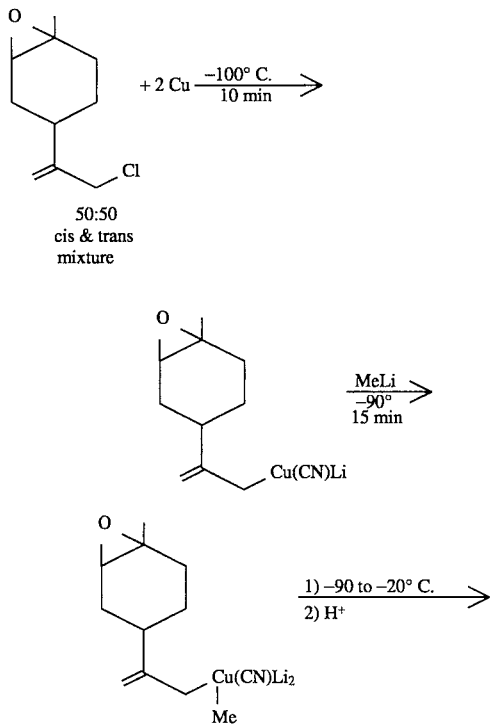

-continued
Scheme 1

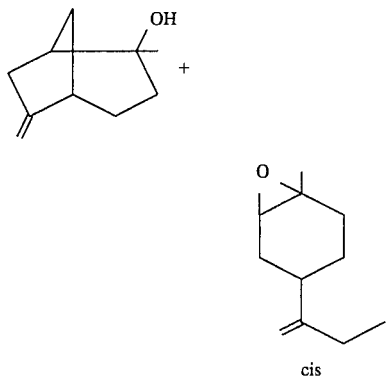

Since the starting ally chloride is a 50:50 mixture of cis and trans epoxides, only half of the available organocopper reagent (the one derived from the trans isomer) has the proper conformation to undergo addition to the epoxide. Moreover, only the cis epoxide (protonated after the reaction was quenched with $NH_4Cl$) along with starting material was isolated after work-up. The product, must have a diaxial orientation between the newly form C—C bond and the hydroxyl group. This is a unique example of both chiral induction into a bicyclic ring system and chiral resolution of a racematic mixture.

TABLE IV
$$\text{Cu} + R_F\text{—}\underset{1.0 \text{ eq.}}{\diagup\!\!\!\diagdown}\!\!\text{—Cl} \xrightarrow[10 \text{ min.}]{-100^\circ \text{ C.}} \xrightarrow[-90^\circ \text{ to } -20^\circ \text{ C.}]{E^+} R_F\!\!\diagup\!\!\!\diagdown\!\!\text{—E}$$
| Allyl Chloride[c] | E[+] | Product | Isolated Yield[d] |
|---|---|---|---|
| 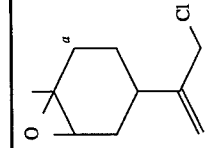 | PhCHO | 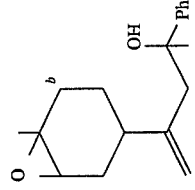 | 94% |
| 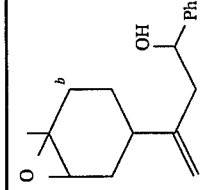 | PhCOCH₃ | 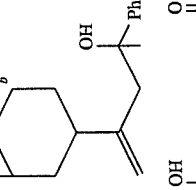 | 90% |
| 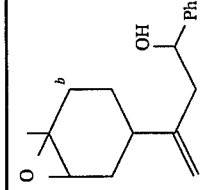 | PhCHO | 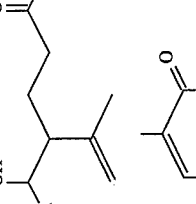 | 62% |
| 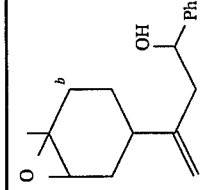 | PhCHO | 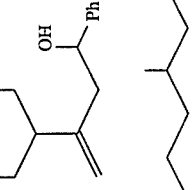 | 67% |
| 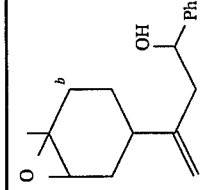 | PhCOCl | 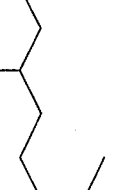 | 70% |

TABLE IV-continued $$\text{Cu} + \text{R}_F\underset{1.0 \text{ eq.}}{\diagup\!\!\!\diagup}\text{Cl} \xrightarrow[10 \text{ min.}]{-100^\circ \text{ C.}} \xrightarrow[-90^\circ \text{ to } -20^\circ \text{ C.}]{\text{E}^+} \text{R}_F\diagup\!\!\!\diagup\text{E}$$

| Allyl Chloride[c] | E[+] | Product | Isolated Yield[d] |
|---|---|---|---|
| [structure with OC(=O)CH₃[b]] | PhCHO | [structure with Ph-C(=O)- and OC(=O)CH₃[b]] | 83% |
| [structure with OC(=O)CH₃[b]] | NCH₂Ph ‖ PhCH | [structure with HNCH₂Ph/Ph and OCCH₃] | 79% |
| [structure with CN[b]] | PhCHO | [structure with Ph-CH(OH)- and CN[b]] | 89% |
| [structure with CH₂CN[b]] | PhCOCl | [structure with Ph-C(=O)- and CN[b]] | 70% |
| [structure with CH₂CN[b]] | [cyclohexanone] | [structure with cyclohexyl-OH and CN[b]] | 65% |

TABLE IV-continued $$\text{Cu} + R_F \xrightarrow[1.0 \text{ eq.}]{} \text{Cl} \xrightarrow[10 \text{ min.}]{-100^\circ \text{ C.}} \xrightarrow[-90^\circ \text{ to } -20^\circ \text{ C.}]{E^+} R_F \diagdown\!\!\diagdown\!\!\diagdown E$$

| Allyl Chloride[c] | E[+] | Product | Isolated Yield[d] |
|---|---|---|---|
| CH$_2$CN[b] structure | Br(exs.) allyl | CN products (ratio of 67:33) | 61% |
| CH$_2$CN structure | Br(lim.) allyl | CN products (ratio of 80:20) | 100% |
| CO$_2$Et structure | PhCHO | CO$_2$Et / OH / Ph product | 73% |
| CH$_2$Cl structure | PhCHO | Cl[b] / OH / Ph product | 65% |
| CH$_2$Cl structure | cyclohexanone | Cl[b] / OH-cyclohexyl product | 51% |

TABLE IV-continued $$\text{Cu} + \text{R}_F \diagup\!\!\!\diagup\!\!\!\diagdown \text{Cl} \xrightarrow[\text{10 min.}]{-100^\circ \text{C.}} \xrightarrow[-90^\circ \text{ to } -20^\circ \text{C.}]{\text{E}^+} \text{R}_F \diagup\!\!\!\diagup\!\!\!\diagdown \text{E}$$
1.0 eq.

| Allyl Chloride[c] | E[+] | Product | Isolated Yield[d] |
|---|---|---|---|
| (structure: CH₂OCON(CH₃)₂ allyl chloride) | PhCHO | (structure with Ph, OH, OCON(CH₃)₂)[b] | 96% |
| (bicyclic structure with Cl)[a] | — | (bicyclic OH structure) | 47%(94%) |

[a]Mixture of cis and trans isomers.
[b]Mixture of diastereoisomers.
[c]Ratio of RCl to active copper is 0.4 to 1.
[d]Yields involving acid chlorides as based on RCl with a three-fold excess of acid chloride used. With other electrophiles, the yields are based on the final electrophile with the RCl to electrophile ratio being 2 to 1, respectively.
[e]The syn isomer was assigned based on the large coupling constant observed for the proton attached to the hydroxyl carbon, J = 9.4 Hz.

Typical Procedure for Reactions of Functionalized Allylic Organocopper Reagents to Aldehydes, Ketones, Imines and Allyl Bromides The functionalized allyl chloride $H_2C=CH(CH_3)-CH_2Cl-CH_2CH_2-CH_2(CH_3)-CH_2CH_2OCON(CH_3)_2$ (2.01 mmol) was weighed into an 8 ml vial, sealed with a septum and placed under argon. THF (4 ml) was added to the vial and the vial was cooled to $-78°$. The allyl chloride was added rapidly to a suspension of the active copper (5.02 mmol) at $-100°$ C. and mixed for 10 min. Benzaldehyde (1.02 mmol) was delivered from a vial in 2 ml of THF to the organocopper solution at $-90°$. The reaction was allowed to warm to $-20°$ C. for 3 hours. The solution was quenched with saturated $NH_4Cl$, extracted with $Et_2O$ (2×50 ml), washed with brine (2×50 ml), and dried over $MgSO_4$. Flash silica gel chromatography, utilizing gradient mixtures of hexane and EtOAc, afforded 6-(hydroxyphenylmethy)-3,7-dimethyl- 7-octenyl N,N-dimethylcarbamate (0.98 mmol, Entry 16 in Table IV). $R_f=0.26$ in 7:3 (v/v) hexane to ethyl acetate, respectively (96% yield): IR (neat) 3442, 3066, 3028, 2954, 2929, 2871, 1707, 1689, 1645, 1495, 1454, 1406, 1373, 1275, 1196, 1063, 1028, 889, 769, 702 cm$^{-1}$. $^1$H NMR (360 MHz) 7.35–7.27 (m, 5H), 5.04 ((s, 1H) and a singlet at 4.73 for a diastereomer), 4.94 ((s, 1H) and a singlet at 4.60 for a diastereomer), 4.54 ((d, J=7.32 Hz, 1H) and a doublet, J=9.34 Hz at 4.38 for a diastereomer), 4.11–3.94 (m, 2H), 2.89–2.39 (m, 6H), 2.28–2.22 (m, 1H), 1.99 (s, 1H), 1.72 ((s, 3H) and a singlet at 1.54 for a diastereomer), 1.55–0.77 (m, 10H). $^{13}$C NMR (50 MHz) 156.5, 144.8, 144.6, 143.5, 142.7, 128.0, 127.7, 127.4, 126.9, 126.8, 126.6, 126.3, 115.5, 115.4, 112.0, 76.1, 75.1, 63.7, 63.6, 63.5, 63.4, 56.0, 55.7, 54.7, 54.6, 36.2, 36.1, 35.9, 35.8, 35.7, 35.6, 35.3, 35.1, 34.5, 34.3, 34.0, 30.0, 29,6, 29.1, 25.9, 25.7, 25.4, 25.3, 20.8, 20.7, 19.6, 19.5, 19.0, 18.7, 18.1, 17.9. Anal. Calcd: C, 72.03; H, 9.37; N, 4.20. Found: C, 71.86; H, 9.22; N, 4.48.

5-(1-Ethenyl-3-hydroxy-4-phenylbutnyl)-2-methyl-2-cyclohexenone (Entry 4, Table IV)

(67% yield): IR (neat) 3438, 3084, 3062, 3028, 2887, 1670, 1493, 1452, 1433, 1383, 1367, 1250, 1109, 1053, 760, 731, 702 cm$^{-1}$. $^1$H NMR (360 MHz) 7.35–7.25 (m, 5H), 6.77–6.72 (m, 1H), 5.02– 4.97 (m, 2H), 4.80 (t, J=6.7 Hz, 1H), 2.72–2.57 (m, 2H), 2.49–2.44 (m, 3H), 2.42–2.23 (m, 3H), 1.78 (s, 3H). $^{13}$C NMR (50 MHz) 199.5, 147.6, 147.5, 144.6, 144.3, 143.9, 135.4, 135.3, 128.4, 127.6, 125.7, 112.5, 72.5, 72.4, 44.6, 43.3, 43.1, 40.8, 40.6, 31.6, 31.4. HRMS [M-H$_2$O]$^+$. Calcd, 238.1358. Found, 238.1367.

3-(3,4-Epoxy-4-methylcyclohexyl)-1-phenyl-3-buten-1-ol (Entry 1, Table IV)

$R_f=0.32$ in 4:1 (v/v) hexane and acetate respectively (94% yield): IR (neat) 3424, 3083, 3062, 3027, 2973, 2929, 2863 cm$^{-1}$. $^1$H NMR (200 MHz) 7.35–7.25 (m, 5H), 4.96–4.89 (m, 2H), 4.78–4.75 (m, 1H), 3.06 ((m, 1H) multiplets also seen at 3.04, 2.98, 2.97), 2.46–2.32 (m, 3H), 2.19–2.01 (m, 2H), 1.86–1.55 (m, 4H), 1.43–1.24 ((m, 4H) including singlets at 1.313, 1.309, 1.30, 1.29). $^{13}$C NMR (125 MHz) 150.04, 150.01, 149.9, 149.6, 144.0, 128.3, 127.4, 125.8, 125.7, 111.7, 111.5, 111.4, 111.3, 72.1, 72.0, 71.9, 71.7, 60.4, 60.3, 59.13, 59.10, 57.6, 57.5, 57.4, 57.3, 45.7, 45.6, 45.3, 45.0, 39.4, 38.7, 34.5, 34.4, 31.5, 30.8, 30.73, 30.68, 30.6, 30.3, 28.7, 28.4, 26.4, 26.1, 24.8, 24.5, 24.2, 24.1, 22.9. Anal. Calcd: C, 79.03; H, 8.58. Found: C, 78.63; H, 8.49.

3-(3,4-Epoxy-4-methylcyclohexyl)-1-methylphenyl-3-buten- 1-ol (Entry 2, Table IV)

$R_f=0.25$ in 4:1 (v/v) hexane and ethyl acetate, respectively (90% yield): $^1$H NMR (500 MHz) 7.42–7.39 (m, 2H), 7.32–7.29 (m, 2H), 7.23–7.20 (m, 1H), 4.85–4.74 (m, 2H), 2.94–2.85 (m, 1H), 2.65–2.59 (m, 1H), 2.47–2.44 (m, 1H), 2.36 (t, J=15.8 Hz, 1H), 2.20– 1.81 (m, 2H), 1.71–1.64 (m, 1H), 1.57–1.02 ((m, 10H) includes four singlets at c.a. 1.55 and 4 singlets c.a. 1.22). $^{13}$C NMR (125 MHz) 150.7, 150.4, 150.0, 149.97, 147.91, 147.88, 147.8, 147.7, 127.97, 127.94, 126.5, 126.47, 126.42, 126.4, 124.72, 124.69, 124.6, 112.9, 112.8, 112.77, 112.5, 73.5, 73.5, 73.4, 73.2, 60.3, 60.0, 59.2, 57.33, 57.30, 57.0, 50.0, 49.7, 49.6, 49.5, 39.1, 38.9, 35.3, 35.0, 31.7, 31.2, 30.9, 30.8, 30.7, 30.33, 30.30, 30.27, 30.2, 30.18, 28.6, 28.4, 26.3, 25.9, 25.1, 24.6, 24.1, 24.0, 22.9, 22.8. Anal. Calcd: C, 79.37; H, 8.88. Found: C, 78.91; H, 8.88.

syn-5-(Hydroxyphenylmethyl)-6-methyl-6-hepten-2-one (Entry 3, Table IV)

$R_f=0.10$ in 4:1 (v/v) hexane to ethyl acetate, respectively (62% yield): IR (neat) 3456, 3066, 3030, 2964, 2933, 2891, 1716, 1645, 1454, 1409, 1028, 893, 726, 702 cm$^{-1}$. $^1$H NMR (360 MHz) 7.38–7.26 (m, 5H), 5.06 (s, 1H), 4.41 (d, J=9.4 Hz, 1H), 2.34–2.12 (m, 4H), 4.95 (s, 3H), 1.73 (s, 3H), 1.43–1.51 (m, 2H). $^{13}$C NMR (50MHz) 208.3, 144.4, 142.3, 128.4 , 127.9, 127.1, 116.3, 75.3, 55.2, 41.3, 29.8, 22.6, 18.1. Anal. Calcd: C, 77.55; H, 8.68. Found: C, 77.69; H, 8.86.

6-(Hydroxyphenylmethyl)-3,7-dimethyl-7-octenyl ethanoate (Entry 6, Table IV)

$R_f=0.22$ in 4:1 (v/v) hexane to ethyl acetate, respectively (83% yield): IR (neat) 3471, 3068, 3030, 2966, 2933, 2873, 1743, 1645, 1454, 1369, 1244, 1051, 1034, 891, 764, 702 cm$^{-1}$. $^1$H NMR (360 MHz) 7.37–7.28 (m, 5H), 5.06–5.05 ((m, 1H) and 4.76 bs), 4.96 ((s, 1H), and singlet at 4.82 for diastereomer), 4.37 (dd, J=9.4 Hz, 1H) and doublets at 4.56 and 4.38; J=7.2 Hz and 9.3 Hz; respectively, for diastereomers), 4.10–3.94 (m, 2H), 2.32–2.22 (m, 1H), 2.02 ((s, 3H) and singlets at 2.01, 1.99, 1.98 for diastereomers), 1.73 ((s, 3H) and singlets at 1.56, 1.55 for diastereomers), 1.70–0.72 (m, 10H). $^{13}$C NMR (50 MHz) 171.0, 170.9, 144.9, 144.8, 144.6, 143.4, 142.6, 128.1, 127.8, 127.5, 127.0, 129.9, 129.8, 126.3, 115.7, 115.6, 113.1, 76.2, 75.2, 67.7, 62.9, 62.8, 62.7, 62.6, 56.1, 55.8, 54.8, 54.6, 35.7, 35.6, 34.8, 34.6, 34.5, 34.3, 34.2, 34.0, 30.0, 29.6, 29.1, 25.8, 25.6, 25.4, 24.3, 25.2, 20.9, 20.8, 20.7, 19.6, 19.5, 19.0, 18.7, 18.1, 17.9.

3,7-Dimethyl-6-(oxophenylmethyl)-7-octenyl ethanoate (Entry 5, Table IV)

$R_f=0.33$ in 4:1 (v/v) hexane to ethyl acetate, respectively (70% yield): IR (neat) 3072, 3026, 2954, 2927, 2871, 1738, 1681, 1641, 1597, 1581, 1448, 1367, 1313, 1273, 1242, 1178, 1111, 1051, 1028, 1003, 955, 899, 771, 739, 714 cm$^{-1}$. $^1$H NMR (360 MHz) 8.05–7.95 (m, 2H), 7.56–7.49 (m, 1H), 7.46–7.40 (m, 2H), 4.92 (s, 2H), 4.11–4.05 (m, 2H), 4.01 (t, J=7.3 Hz, 1H), 2.03 ((s, 2H), and a singlet at 2.01 for a diastereomer), 1.71– 1.70 (m, 3H), 1.62–1.08 (m, 7H), 0.95–0.91 (m, 3H). $^{13}$C NMR (50MHz) 200.1, 171.0, 143.3, 143.2, 137.0, 132.7, 129.4, 128.4, 128.3, 128.2, 114.8, 114.7, 62.8, 55.3, 35.3, 35.2, 34.7, 29.9, 29.8, 27.5, 27.3, 20.9, 20.0, 19.9, 19.3, 19.2. Anal. Calcd: C, 75.46; H, 8.67. Found: C, 75.82; H, 8.81.

3,7-Dimethyl-6-[(phenylmethylamido)phenylmethyl]-7-octenyl ethanoate (Entry 7, Table IV)

$R_f=0.35$ in 4:1 (v/v) hexane and ethyl acetate, respectively (79% yield): IR (neat) 3062, 3026, 2956, 2929, 2871, 1739, 1495, 1454, 1365, 1242, 1053, 1028, 893, 766, 737, 700 cm$^{-1}$. $^1$H NMR 360 MHz) 7.33–7.18 (m, 10H), 4.96 ((d, J=1.5 Hz, 1H) and a doublet at 4.68, J=1.5 Hz for a diastereomer), 4.92 ((s, 1H) and a singlet at 4.55 for a diastereomer), 4.07–4.00 (m, 2H), 3.66–3.62 (m, 1H), 3.56 (d, J=7.5 Hz, 1H), 3.45–3.41 (m, 1H), 2.27–2.18 (m, 1H), 2.11–2.01 (m, 3H), 1.90–1.52 (m, 4H), 1.47 (s, 3H), 1.44–1.05 (m, 4H), 0.86 (t, J=6.7 Hz, 3H). $^{13}$C NMR (50 MHz) 171.1, 145.1, 145.0, 142.9, 140.7, 128.2, 128.0, 127.9, 127.8, 126.7, 126.6, 113.1, 113.0, 64.6, 63.0, 54.2, 54.0, 51.5, 35.8, 34.9, 34.6, 30.1, 29.7, 25.8, 25.8, 25.7, 20.9, 20.7, 20.6, 19.7, 19.1. Anal. Calcd: C, 78.70; H, 9.25; N, 3.67. Found: C, 78.73; H, 9.08; N, 3.51.

7-(Hydroxyphenylmethyl)-4,8-dimethyl-8-nonenonitrile (Entry 8, Table IV)

$R_f$=0.13 in 4:1 (v/v) hexane and ethyl acetate, respectively (89% yield): IR (neat) 3485, 3066, 3027, 2956, 2929, 2871, 2245, 1735, 1643, 1495, 1454, 1425, 1375, 1243, 1047, 1028, 893, cm$^{-1}$ $^1$H NMR (500 MHz) 7.35–7.22 (m, 5H), 5.04 (m, 1H), 4.95–4.61 (m, 1H), 4.53–4.36 (m, 1H), 2.31–2.14 (m, 4H), 1.72 (s, 3H), 1.69–0.93 ((m, 7H) including a singlet at 1.54), 0.87 ((d, J=6.45 Hz, 3H) also doublets for diastereomers at 0.85 (J=6.44 Hz), 0.74 (J=6.85 Hz) and 0.72 (J=6.44 Hz)). $^{13}$C NMR (125 MHz) 144.8, 144.7, 144.6, 144.5, 143.2, 142.5, 142.4, 128.2, 127.9, 127.6, 127.1, 126.9, 126.3, 119.8, 119.7, 119.6, 116.0, 115.8, 113.2, 113.1, 77.3, 77.0, 76.8, 76.0, 75.2, 56.0, 55.8, 54.6, 54.4, 33.8, 33.6, 33.5, 33.4, 32.4, 32.3, 32.0, 31.8, 31.6, 31.4, 31.3, 25.6, 25.5, 25.0, 24.9, 21.0, 20.9, 18.9, 18.7, 18.4, 18.1, 17.9, 14.7, 14.6, 14.5. Anal Calcd: C, 79.66; H, 9.28; N, 5.16. Found: C, 79.48; H, 9.03; N, 5.50.

4,8-Dimethyl-7-(oxophenylmethyl)-8-nonenonitrile (Entry 9, Table IV)

$R_f$=0.10 in 9:1 (v/v) hexane and ethyl acetate, respectively (70% yield): IR (neat) 3070, 2956, 2931, 2871, 2245, 1682, 1641, 1597, 1579, 1448, 1378, 1269, 1234, 1203, 901 cm$^{-1}$. $^1$H NMR (200 MHz) 8.00–7.96 (m, 2H), 7.58–7.39 (m, 3H), 4.93 (m, 2H), 4.03 ((t, J=7.2 Hz, 1H) also a triplet at 4.02), 2.34 ((t, J=7.2 Hz, 2H) also a triplet at 2.32), 2.03–1.12 (m, 10H), 0.94 ((d, J=6.3 Hz, 3H) also a doublet at 0.92). $^{13}$C NMR (50 MHz) 199.9, 143.1, 142.9, 136.80, 136.76, 132.7, 128.3, 128.2, 119.74, 119.71, 114.9, 114.7, 55.0, 33.8, 33.7, 31.9, 31.8, 31.7, 27.1, 27.0, 20.0, 19.8, 18.6, 14.6, 14.59. Anal. Calcd: C, 80.26; H, 8.61; N, 5.20. Found: C, 80.07; H, 8.70; N, 5.17.

7-(1-Hydroxycyclohexyl)-4,8-dimethyl-8-nonenonitrile (Entry 10, Table IV)

$R_f$=0.23 in 4: 1 (v/v) hexane and ethyl acetate, respectively (65% yield): $^1$H NMR (300 MHz) 4.93 (m, 1H), 4.75–4.74 (m, 1H), 2.36–2.29 (m, 2H), 1.95– 1.91 (m, 1H), 1.75 ((s, 3H) also a singlet at 1.74 for other diastereomer), 1.72–1.12 (m, 18H), 0.92 ((d, J= 6.44 Hz, 3H) and a doublet at 0.92, J=6.43 Hz, for the other diastereomer). $^{13}$C NMR (75 MHz) 145.7, 145.6, 119.9, 114.2, 114.1, 72.6, 72.5, 57-3, 56.8, 36–2, 36.0, 35.9, 34.6, 34.2, 32.6, 32.3, 31.9, 31–8, 25.8, 23.9, 23.6, 22.1, 22.0, 21.9, 19.1, 18.6, 14.9, 14.8.

4,8-Dimethyl-7,11-dodecadienonitrile (Major Isomer, Entry 11, Table IV)

$R_f$=0.42 in 9:1 (v/v) hexane and ethyl acetate, respectively. $^1$H NMR (500 MHz) 5.84–5.77 (m, 1H), 5.11 (m, 1H), 5.04–5.01 (m, 1H), 4.96–4.94 (m, 1H), 2.39– 2.29 (m, 2H), 2.17–1.94 (m, 5H), 1.71–1.68 (m, 3H), 1.67– 1.56 (m, 2H), 1.51–1.44 (m, 2H), 1.38–1.31 (m, 1H), 1.22– 1.16 (m, 1H), 0.92 (d, J=6.45 Hz, 3H). $^{13}$C NMR (125 MHz) 138.4, 134.9, 125.0, 119.8, 114.5, 36.5, 32.2, 32.1, 31.6, 31.2, 24.9, 23.2, 18.6, 14.8. HRMS for C$_{14}$H$_{23}$N calcd. 205.1831. Found, 205.1825.

4-Methyl-7-(1-methylethenyl)-9-decenonitrile (Minor Isomer, Entry 11, Table IV)

$R_f$=0.55 in 9:1 (v/v) hexane and ethyl acetate, respectively. $^1$H NMR (500 MHz) 5.85– 5.80 (m, 1H), 5.21–5.20 (m, 1H), 5.17 (s, 1H), 4.70 (s, 1H), 4.67 (s, 1H), 2.67–2.64 (m, 1H), 2.36–2.31 (m, 2H), 2.12–1.99 (m, 2H), 1.71 ((s, 3H) also a singlet at 1.69), 1.54–1.23 (m, 7H), 0.95 ((d, J=6.85 Hz, 3H) also a doublet at 0.92, J=6.45 Hz for the other diastereomer). $^{13}$C NMR (125 MHz) 145.7, 145.6, 133.2, 133.1, 121.9, 121.6, 118.8, 118.7, 110.0, 109.9, 39.1, 39.0, 38.9, 37.8, 36.9, 36.8, 36.4, 35.3, 30.8, 30.6, 29.5, 29.3, 24.7, 24.5, 22.2, 19.7, 18.8.

Ethyl 6-(hydroxyphenylmethyl)-3,7-dimethyl-7-octenoate (Entry 13, Table IV)

$R_f$=0.31 in 4: 1 (v/v) hexane and ethyl acetate, respectively (73% yield): $^1$H NMR (300 MHz) 7.36–7.21 (m, 5H), 5.04 (m, 1H), 4.94 ((m, 1H) also sharp multiplets at 4.75 and 4.60 for other diastereomers), 4.36 ((dd, J=9.29, 1.66 Hz, 1H) also add at 4.53 (J=7.15, 1.67 Hz)), 4.06 ((q, J=7.15 Hz, 2H) amidst quartets for other diastereomers), 2.41–1.88 (m, 5H), 1.71 (s, 3H), 1.54 (s, 1H), 1.28–0.96 (m, 6H), 0.78 ((d, J=6.43 Hz, 3H) doublets also at 0.93, 0.88, 0.75 with J coupling 7.15, 6.91 and 6.68 Hz, respectively. $^{13}$C NMR (75 MHz) 173.2, 173.1, 173.0, 172.9, 146.03, 146.0, 144.8, 144.7, 144.6, 144.5, 143.3, 142.5, 128.2, 128.1, 127.9, 127.6, 127.3, 127.1, 126.9, 126.3, 125.6, 116.0, 115.9, 113.2, 113.1, 112.7, 112.6, 76.1, 76.0, 75.2, 75.1, 71.6, 71.5, 59.9, 56.1, 55.9, 54.6, 54.4, 46.5, 41.9, 41.7, 41.6, 41.3, 41.0, 36.1, 36.0, 35.7, 35.6, 34.3, 34.1, 33.9, 30.5, 30.2, 30.1, 30.08, 30.03, 29.8, 25.8, 25.6, 25.0, 24.8, 24.7, 21.0, 20.9, 19.9, 19.8, 19.6, 19.5, 19.3, 19.0, 18.0, 17.9, 14.1. Anal. Calcd: C, 74.96; H, 9.27. Found: C, 74.74; H, 9.56.

2-(5-Chloro-3-methylphenyl)-1-phenyl-3-buten-1-ol (Entry 14, Table IV)

$R_f$=0.41 in 4:1 (v/v) hexane and ethyl acetate, respectively (65% yield): $^1$H NMR (500 MHz) 7.35– 7.23 (m, 5H), 5.05 (m, 1H), 4.96 ((m, 1H) also multiplets for diastereomers at 4.74, 4.61), 4.36 (d, J=8.46, 1H), 3.49–3.37 ((m, 2H), 2.31–2.25 (m, 2H), 1.72 (s, 3H), 1.69–0.90 (m, 7H), 0.73 ((d, J=6.85 Hz, 3H) doublets for other diastereomers at 0.71, 0.87, 0.85 with J values 6.05, 6.44, 6.45 Hz, respectively. Ratios from integration of diastereomers equal 4.3, 3.2, 1, 1. $^{13}$C NMR (125 MHz) 144.8, 144.6, 142.5, 128.2, 128.0, 127.7, 127.2, 127.0, 126.3, 116.1, 116.0, 76.1, 75.2, 75.1, 56.1, 55.9, 43.1, 39.9, 38.9, 34.0, 33.9, 33.8, 30.0, 29.6, 25.7, 25.6, 19.2, 19.1, 18.4, 18.0, 17.9. Anal. Calcd: Calcd: C, 72.71; H, 8.97; Cl, 12.62. Found: C, 72.47; H, 9.14; Cl, 12.63.

1-Chloro-6-(1-hydroxycyclohexyl)-3,7-dimethyl-7-octene (Entry 15, Table IV)

$R_f$=0.52 in 4:1 (v/v) hexane and ethyl acetate, respectively (51% yield): $^1$H NMR (200 MHz) 4.92 (m, 1H), 4.74 (m, 1H), 3.56–3.50 (m, 2H), 1.99–1.07 ((m, 18H) including a singlet at 1.75 (3H)), 0.90 ((d, J=6.15 Hz, 3H) also a doublet at 0.89 (J=6.02) for the other diastereomer). $^{13}$C NMR (50 MHz) 145.7, 145.6, 114.1, 72.6, 72.5, 57.9, 56.9, 43.2, 40.0, 39.3, 36.2, 36.1, 35.8, 35.0, 34.6, 30.7, 30.2, 25.8, 23.9, 23.7, 22.6, 22.1, 22.0, 19.4, 18.8. Anal. Calcd: C, 70.43; H, 10.71; Cl, 12.99. Found: C, 70.39; H, 10.85; Cl, 13.23.

Intramolecular Epoxide Ring Opening Reaction

The procedure for intramolecular epoxide ring opening reaction was the same as that carried out for the intermolecular epoxide opening reaction already described. 6-Ethyl-2-hydroxy-2-methylbicyclo[3.2.1]octane (Entry 17, Table IV). $R_f$=0.22 in 4:1 (v/v) hexane and ethyl acetate, respectively (97% yield based on available isomer): m.p. 85.5°–88.0° C. uncorrected. $^1$H NMR (360 MHz) 4.89 (s, 1H), 4.83 (s, 1H), 2.56 (s, 1H), 2.41–2.32 (m, 1H), 2.17–2.12 (m, 1H), 2.07–2.03 (m, 2H), 1.80–1.71 (m, 1H), 1.57–1.30 (m, 5H), 1.18 (s, 3H). $^{13}$C NMR (50 MHz) 154.2, 104.4, 72.7, 46.5, 41.3, 35.5, 33.7, 32.3, 30.2, 29.2. Anal. Calcd: C, 78.81; H, 10.59. Found: C, 78.77; H, 10.80.

EXAMPLE 6

The reaction of 2-chloroallyl acetate with active copper derived from CuCN.2LiCl allows for the formation of the biscuprate, i.e., bis organocopper reagent, (Compound 1 in Scheme 2). Table V shows typical examples of bis organocopper reagents that could be prepared using either this method or that outlined below in Example 7 using the zerovalent active copper of the present invention.

Because the allylic organocopper moiety is more reactive than the vinyl copper moiety, one can selectively add an electrophile to the allylic segment then add another electrophile to the vinyl copper segment. Thus, to a solution of active copper (1 equiv) was added 2-chloroallyl acetate (0.25 equiv) at –100° C. for 20 minutes producing the biscuprate (1). The reaction of (1) with benzaldehyde at –78° C. followed by addition of $I_2$ allowed for the production of (2) in good yield.

Scheme 2

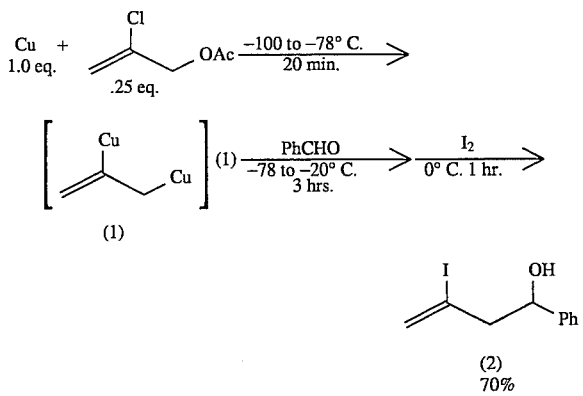

TABLE V

Bis Organocopper and Propargyl Reagents

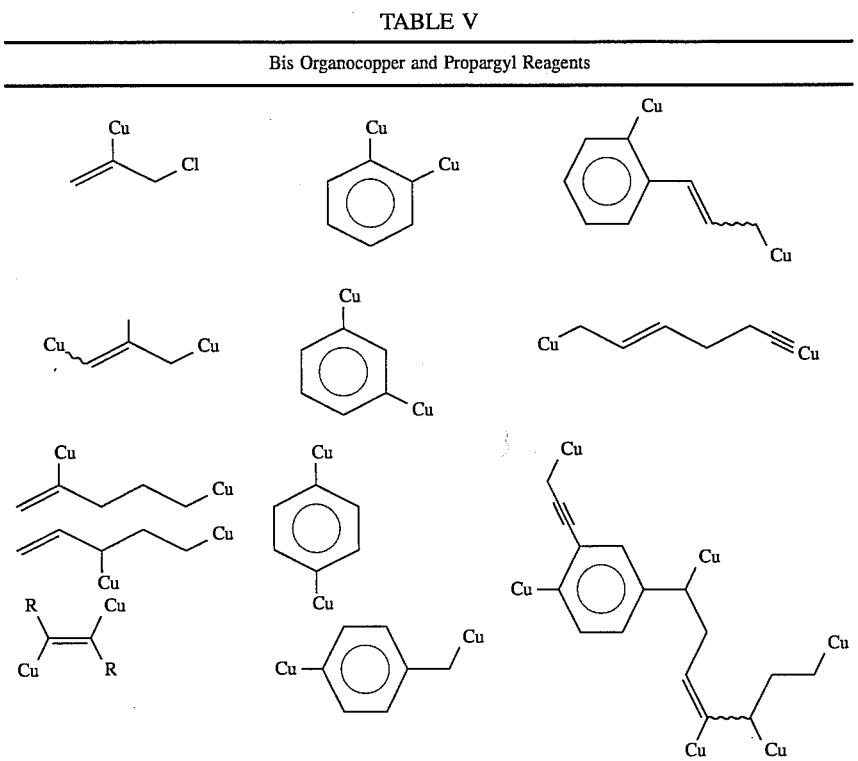

TABLE V-continued

Bis Organocopper and Propargyl Reagents

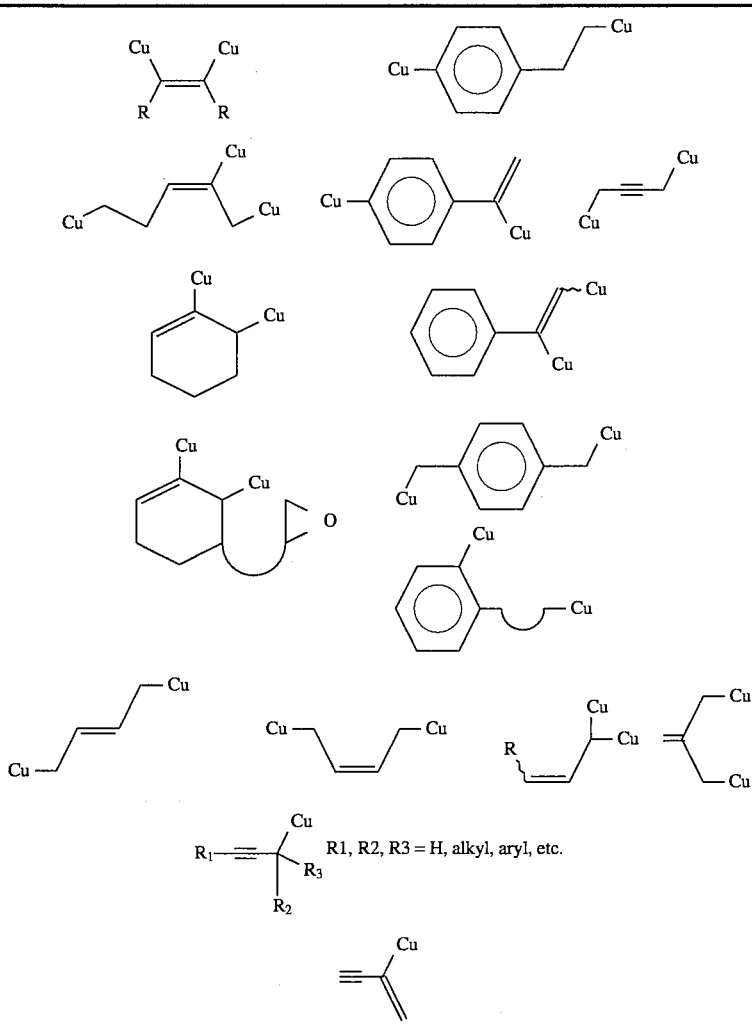

[1] If bis complexes are formed on identical hybridized carbons, two identical electrophiles can be used.
[2] If bis copper complexes are formed on different hybridized carbons, electrophiles can be selectively added.

EXAMPLE 7

A variety of bis organocopper reagents can be formed using the following method. 2,3-Dichloropropene (3.02 mmol) was placed in a septa covered vial, mixed with 2 ml of THF, cooled to −78° C. and transferred via cannula to the active copper solution prepared by method B of Example 1 at −100° C. The resulting heterogenous solution was allowed to warm to −78° C. over the course of 15 minutes to produce the bis organocopper reagent (1).

These bis organocopper reagents can be used in organic synthesis as follows. To the bis organocopper reagent prepared from 2,3-dichloropropene, was added PhCHO (1.02 mmol) via cannula. The mixture was then warmed to −20° C. and held at this temperature for 3 hours. Allyl bromide (6.14 mmol) was then added neat via disposable syringe at −20° C., warmed to 0° C., and held at 0° C. for one hour. The solution was then quenched with 5 ml of NH$_4$Cl(sat.), washed with brine, extracted with Et$_2$O, and dried over MgSO$_4$. The solvents were removed under vacuum and the resulting crude mixture was separated via flash silica gel chromatography using mixtures of hexanes and ethyl acetate to afford 136.3 mg of product, 71%. Table VI shows representative examples.

TABLE VI

| $E_1$ | $E_2$ | Product | % Yield[a] |
|---|---|---|---|
| PhCHO | H[+] | | 84 |
| PhCHO | allyl-Br | | 71 |
| PhCHO | $I_2$ | | 69 |
| 5-oxohexanenitrile | $I_2$ | | 32 |
| 5-oxohexanenitrile | allyl-Br | | 54 |

[a]Isolated yields

TABLE VII

Intramolecular Organocopper Reactions

A. Preparation of ketone and aldehyde containing cuprates which will undergo 1,2 addition reactions to form novel cyclic molecules.

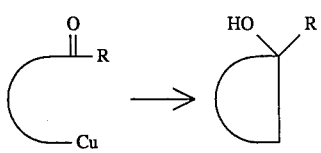

B. Other examples:

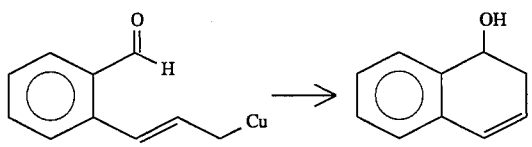

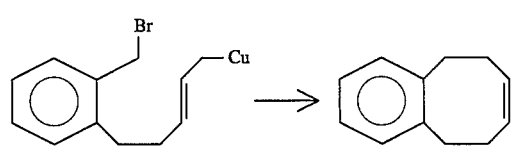

TABLE VII-continued

Intramolecular Organocopper Reactions

C. Other examples involving epoxides.

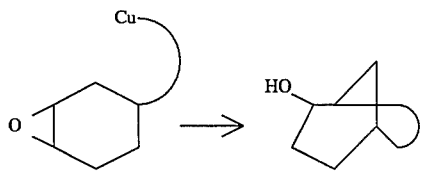

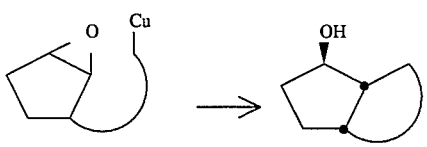

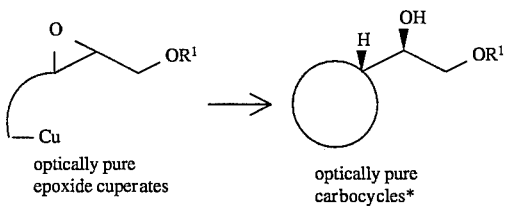

optically pure epoxide cuperates → optically pure carbocycles*

TABLE VII-continued

Intramolecular Organocopper Reactions

D. Intramolecular 1,4 Conjugate Additions

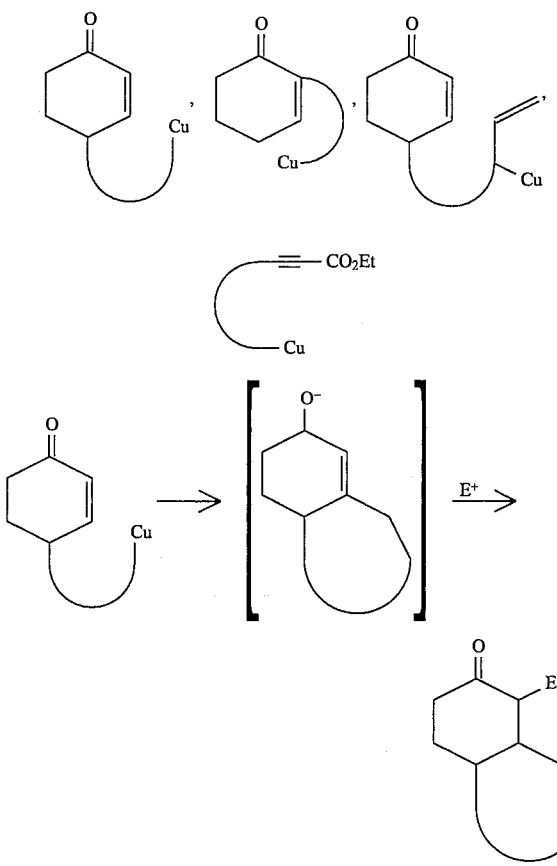

E. Intramolecular Reactions with bis-organocuprates

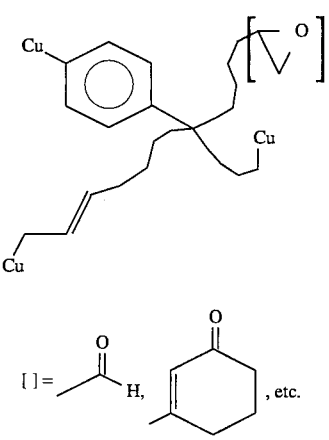

TABLE VII-continued

Intramolecular Organocopper Reactions

*This would be a general approach to chiral substrates which is of a major concern to drug companies today.

TABLE VIII

Aryl & Alkylaryl Copper Reagents

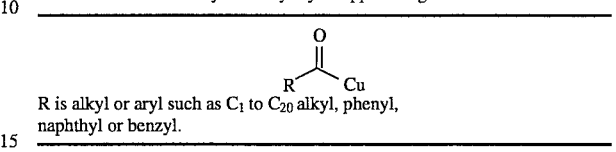

R is alkyl or aryl such as $C_1$ to $C_{20}$ alkyl, phenyl, naphthyl or benzyl.

TABLE IX

Deoxygenation of Sulfides, Sulfones and Sulfonates

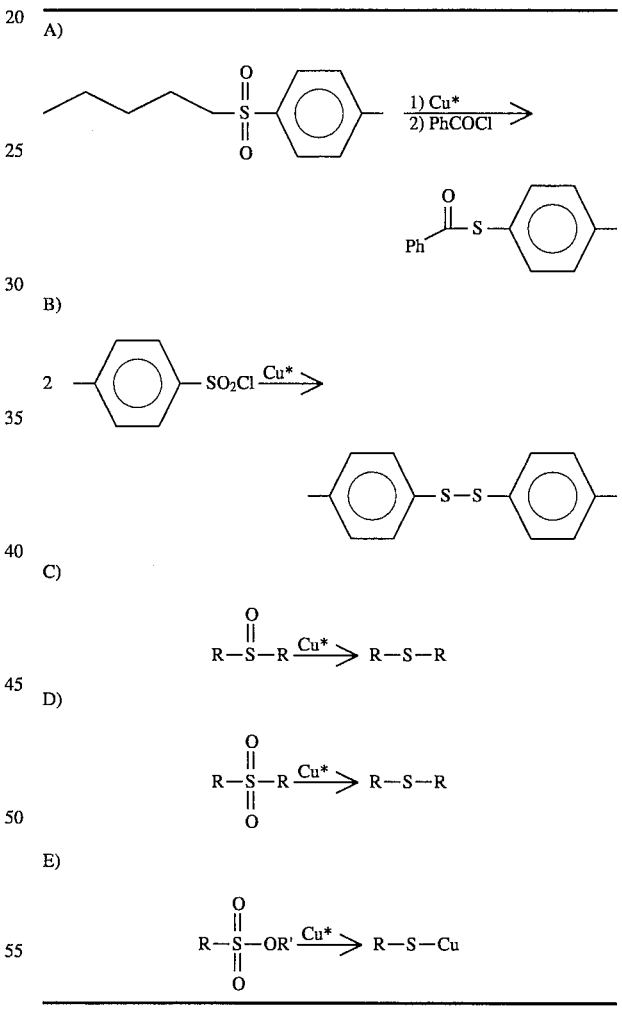

TABLE X

Heterocyclic Cuprates

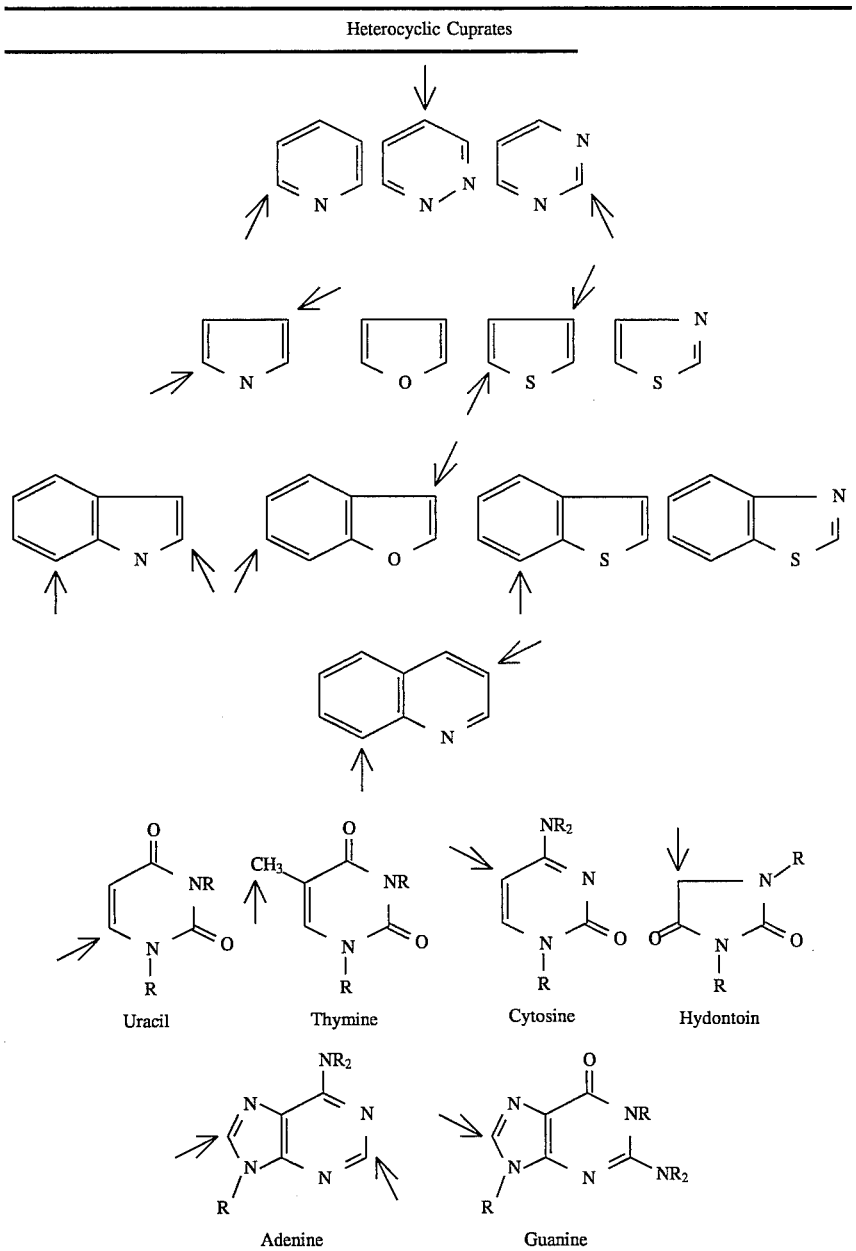

The copper can be substituted at any position capable of being substituted by a halogen. Some examples of such copper substitutions are indicated by arrows on the above structure.

EXAMPLE 8

The active copper made from the reduction of a lithium 2-thienylcyanocuprate solution, oxidatively adds to allyl chlorides and acetates at low temperatures to allow the direct formation of allylic organocopper reagents without Wurtz-like homocoupling products. Specifically, the thienyl-based copper reacts with allyl chlorides and acetates at −100° C. to produce the corresponding allylic organocopper species with less than 5% of the homocoupled diene by-product and occasionally accompanied with less than 2% of the thienyl ligand transfer side product.

The resulting allylic organocopper reagents were subsequently trapped with benzoyl chloride to produce the corresponding ketones, Table XI. The allylic organocopper reagents react with the acid chloride at the gamma position, Table XI, Entry 1. Since it is known that prenyl copper reacts with cyclohexenone at the alpha position, it is presumed that the secondary allyl chloride (Table XII, Entry 2) also involves gamma attack, only after the organocopper rearranges to the more favorable primary allylic structure.

The effect of the reduction temperature in determining the reactivity of the active copper is shown in Table XII. The optimum conditions for product formation occurs when the lithium 2-thienylcyanocuprate solution is reduced at −78° C. or lower, followed by the addition of the allylic substrate at less than −100° C., preferably at −108° C., and subsequently trapped with the electrophile at less than −90° C., preferably at −95° C. The allylic organocopper reagents also react with benzaldehyde to give the corresponding alcohol in moderate yields, Table XIII. The reaction of 3-chloro-1-butene with benzaldehyde gives a 66:34 syn to anti diastereomer mixture of the homoallylic alcohol product, Table XIII, Entry 2.

TABLE XI

Reactions of Allylic Thienyl-Based Organocopper Reagents with Benzoyl Chloride

| Entry | Allyl Chloride/Acetate[a] | Product[b] | % Yield[c] |
|---|---|---|---|
| 1 | (prenyl chloride) | (2,2-dimethyl-1-phenyl-but-3-en-1-one) | 56 |
| 2 | (3-chloro-1-butene) | (2-methyl-1-phenyl-but-3-en-1-one) | 40 |
| 3 | (methallyl chloride) | (3-methyl-1-phenyl-but-3-en-1-one) and (2-methylallyl thiophene) | 55 and 2 |
| 4 | (allyl acetate) | (1-phenyl-but-3-en-1-one) | 46 |

[a]To a solution of active copper at −100° C. was added the allyl chloride (0.25 equiv). Three equiv of Benzoyl Chloride (based on the organocopper) was added neat via syringe at −95° C.
[b]All products had consistent $^1$H, $^{13}$C NMR spectra.
[c]Isolated yields.

TABLE XII

Formation and Reaction of Prenyl Copper with Benzoyl Chloride at Various Temperatures 1.05 Li[+] (naphthalene) + (thienyl-CuCN-Li) $\xrightarrow[T_1]{THF}$ 1.0 Cu Cu + 0.25 (prenyl chloride) $\xrightarrow[T_2]{THF}$ $\xrightarrow[T_3]{PhCOCl}$ (2,2-dimethyl-1-phenyl-but-3-en-1-one)

| $T_1$ | $T_2$ | $T_3$ | % Yield[a] |
|---|---|---|---|
| −108 | −108 | −95 | 65 |
| −78 | −108 | −95 | 65 |
| −50 | −108 | −95 | 51 |
| −50 | −50 | −50 | 37 |

[a]Quantitation by GC analysis with authentic samples and using decane as an internal standard.

TABLE XIII

Reactions of Allylic Thienyl-Based Organocopper Reagents with Benzaldehyde

| Entry | Allyl Chloride/Acetate[a] | Product[b] | % Yield[c] |
|---|---|---|---|
| 1 | (CH₃)₂C=CH-CH₂-Cl (prenyl chloride) | PhCH(OH)-C(CH₃)₂-CH=CH₂ | 80 |
| 2 | CH₂=CH-CH(CH₃)-Cl | PhCH(OH)-CH(CH₃)-CH=CH₂ | 70[d] |
| 3 | CH₂=C(CH₃)-CH₂-Cl | PhCH(OH)-CH₂-C(CH₃)=CH₂ | 78 |
| 4 | CH₂=CH-CH₂-OAc | PhCH(OH)-CH₂-CH=CH₂ | 26 |
| 5 | CH₂=CH-CH₂-Cl | PhCH(OH)-CH₂-CH=CH₂ | 61 |

[a]The ratio between the allyl chloride and active copper was 0.4:1.
[b]Ratio of the organocopper to the electrophile was 2:1. All products had consistent $^1H$ and $^{13}C$ NMR spectra.
[c]Isolated yields are based on the electrophile.
[d]A 66:34 syn to anti diastereomer mixture as observed by NMR.

Reaction of Allylic Organocopper Reagents with Benzoyl Chloride

4-Chloro-2-methyl-2-butene (2.00 mmol) was weighed into a vial and sealed with a septum. Using a freeze-pump-thaw technique, air was removed and replaced with argon. THF (4 ml) was added to the vial and then cooled to −78° C. The allyl chloride was then cannulated to the active copper solution (8.00 mmol) at −108° C. The solution was stirred at −108° C. for 10 minutes and then warmed to −95° C. Benzoyl chloride (8.80 mmol) and decane (2.00 mmol) were admixed with 4 ml of THF in a vial, cooled to −78° C. and then cannulated to the organocopper solution at −95° C. The reaction mixture was allowed to warm to −78° C. and stirred for 30 minutes. The solution was then quenched with saturated $NH_4Cl_{(aq)}$, extracted with ether (3×20 ml), washed with brine (3×50 ml), and the organic layer dried over $MgSO_4$. Flash silica gel chromatography using hexanes afforded 2,2-dimethyl-1-phenyl-3-butene-1-one (1.12 mmol), for a 56% yield: IR (neat) 3085, 3059, 2975, 2934, 2872, 1679, 1635, 1597, 1578, 1466, 1412, 1380, 1363, 1259, 1173, 1157, 1001, 971, 918, 796, 719, 694, 667. $^1H$ NMR (300 MHz) 7.85–7.89 (m, 2H), 7.32–7.46 (m, 3H), 6.11–6.26 (dd, $J_1$=17.52 Hz, $J_2$=10.63 Hz, 1H), 5.17–5.27 (m, 2H), 1.39 (s, 6H). $^{13}C$ NMR (300 MHz) 204.5, 143.8, 137.1, 131.5, 129.1, 127.8, 113.9, 50.1, 25.9.

2-Methyl-1-phenyl-3-butene-1-one

IR (neat) 3081, 3060, 2975, 2931, 2871, 1687, 1633, 1596, 1448, 1371, 1334, 1263, 1216, 963, 962, 919, 754, 703, 688. $^1H$ NMR (300 MHz) 7.9–8.00 (m, 2H), 7.41–7.56 (m, 3H), 5.91–6.09 (m, 1H), 5.10–5.22 (m, 2H), 4.14–4.21 (quin., 1 H), 1.32–1.35 (d, 3H). $^{13}C$ NMR (300 MHz) 201.3, 138.1, 136.3, 132.9, 128.6, 128.5, 116.5, 45.5, 17.0.

3-Methyl-1-phenyl-3-butene-1-one

IR (neat) 3076, 2971, 2935, 2913, 1687, 1596, 1579, 1448, 1375, 1332, 1276, 1207, 1180, 1002, 962, 894, 752, 690, 588. $^1H$ NMR (300 MHz) 7.96–7.99 (m, 2H), 7.41–7.55 (m, 3H), 4.98 (s, 1H), 4.85 (s, 1H), 3.68 (s, 2H), 1.82 (s, 3H). $^{13}C$ NMR (300 MHz) 197.9, 139.6, 136.7, 132.9, 128.4, 128.2, 114.8, 47.5, 22.7.

1-Phenyl-3-butene-1-one

IR (neat) 3087, 3070, 3033, 2983, 2944, 2881, 1729, 1600, 1452, 1315, 1278, 1176, 1112, 1070, 1025, 995, 971, 935, 713. $^1H$ NMR (300 MHz) 8.04–8.10 (m, 2H), 7.38–7.59 (m, 3H), 5.94–6.11 (m, 1H), 5.24–5.46 (m, 2H), 4.80–4.84 (d, 2H). $^{13}C$ NMR (300 MHz) 166.2, 132.9, 132.2, 130.2, 129.6, 128.3, 118.1, 65.4.

Reaction of Allylic Organocopper Reagents with Benzaldehyde

4-Chloro-2-methyl-2-butene (3.2 mmol) was weighed into a vial and sealed with a septum. Using a freeze-pump-thaw technique, air was removed and replaced with argon. THF (4 ml) was added to the vial and then cooled to −78° C. The allyl chloride was then cannulated to the active copper solution (8.00 mmol) at −108° C. The solution was stirred at −108° C. for 10 minutes and then warmed to −78° C. Benzaldehyde (1.60 mmol) and decane (3.20 mmol) were admixed with 4 ml of THF in a vial, cooled to −78° C. and then cannulated to the organocopper solution at −78° C. and stirred for 30 minutes. The solution was then quenched with saturated $NH_4Cl_{(aq)}$, extracted with ether (3×20 ml), washed with brine (3×50 ml), and the organic layer dried over $MgSO_4$. Flash silica gel chromatography using gradient mixtures of hexanes/EtOAc afforded 2,2-dimethyl-1-phenyl-3-butene-1-ol (1.28 mmol), for an 80% yield: IR (neat) 3451, 3083, 3062, 3029, 2964, 2929, 2869, 1637, 1452, 1413, 1378, 1361, 1187, 1024, 998, 730, 701. $^1$H NMR (300 MHz) 7.24– 7.28 (m, 5H), 5.84–5.93 (dd, $J_1$=17.41 Hz, $J_2$=10.73 Hz, 1H), 5.00–5.12 (m, 2H), 4.37 (s, 1H), 2.23 (s, 1H), 0.98 (s, 3H), 0.93 (s, 3H). $^{13}$C NMR (300 MHz) 144.9, 140.6, 127.7, 127.3, 113.6, 80.4, 42.0, 24.2, 20.9.

2-Methyl-1-phenyl-3-butene-1-ol

IR (neat) 3400, 3062, 3027, 2973, 2929, 2871, 1639, 1492, 1454, 1415, 1020, 914, 761, 701. $^1$H NMR (300 MHz) 7.22–7.35 (m, 5H), 5.66– 5.84 (m, 1H), 5.12–5.19 (m, 1.7H), 4.98–5.04 (m, 0.806H), 4.53–4.54 (d, J=5.73 Hz, 0.374H), 4.30–4.33 (d, J=7.63 Hz, 0.861H), 2.41–2.55 (m, 2H), 2.35 (s, 1H), 0.85–0.86 (d, 1.93H), 0.83–0.84 (d, 3H). $^{13}$C NMR (300 MHz) 142.7, 142.4, 140.5, 140.3, 128.1, 127.9, 127.5, 127.2, 126.7, 126.4, 116.5, 115.3, 77.7, 77.2, 46.0, 44.5, 16.4, 14.0.

3-Methyl-1-phenyl-3-butene-1-ol

IR (neat) 3396, 3073, 3029, 2967, 2935, 2915, 1646, 1452, 1375, 1054, 1027, 890, 755, 700, 549. $^1$H NMR (300 MHz) 7.2–7.24 (m, 5H), 4.83– 4.90 (d, 2H), 4.76–4.80 (t, 1H), 2.40–2.42 (d, 2H), 2.23 (s, 1H), 1.77 (s, 3H). $^{13}$C NMR (300 MHz) 144.0, 142.3, 128.3, 127.4, 125.7, 113.9, 71.4, 48.2, 22.2.

1-Phenyl-3-butene-1-ol

IR (nat) 3380, 3075, 3064, 3029, 2977, 2929, 1641, 1492, 1454, 1440, 1432, 1415, 1390, 1357, 1315, 1197, 1076, 1047, 1029, 1000, 916, 871, 757, 700. $^1$H NMR (300 MHz) 7.23–7.36 (m, 5H), 5.73–5.86 (m, 1H), 5.10–5.18 (m, 2H), 4.69–4.73 (t, 1H), 2.47–2.53 (m, 2H), 2.17 (s, 1H). $^{13}$C NMR (300 MHz) 143.8, 134.4, 128.3, 127.5, 125.8, 118.3, 73.3, 43.7.

What is claimed is:

1. A zerovalent copper species consisting essentially of a combination of zerovalent copper metal atoms, an alkali metal salt of cyanide, an alkali metal salt of a halide and an alkali metal salt of an aromatic anion.

2. The zerovalent copper species of claim 1 wherein the zerovalent copper metal atoms are in combination with lithium cyanide and a lithium halide.

3. The zerovalent copper species of claim 2 wherein the lithium halide is selected from the group consisting of lithium bromide and lithium chloride.

4. A zerovalent copper species prepared by the reaction of a reducing agent having a reduction potential at least about 100 mV more negative than that of Cu(I) or Cu(II) with a complex of a copper halide or cyanide and an alkali metal salt of a halide.

5. The zerovalent copper species prepared by the method of claim 4 wherein the reducing agent reacts with a complex of a copper(I) halide and a lithium halide or a copper(I) cyanide and a lithium halide.

6. A method for preparation of a zerovalent copper species comprising contacting a complex of a copper halide or cyanide and an alkali metal halide salt with a reducing agent having a reduction potential at least about 100 mV more negative than that of Cu(I).

7. The method of claim 6 wherein a complex of a copper(I) cyanide and a lithium halide is reduced.

8. The method of claim 6 wherein the reducing agent is an alkali metal salt of an aromatic anion, an alkaline earth metal salt of an aromatic anion, an alkali metal, an alkaline earth metal, or an alkali metal hydride.

9. The method of claim 8 wherein the reducing agent is an alkali metal salt of an aromatic anion, and the salt is selected from the group consisting of the lithium salts of naphthalenide, biphenylide, or anthracenylide.

10. The method of claim 6 wherein a complex of a copper(II) halide or cyanide and an alkali metal halide salt is contacted with a reducing agent having a reduction potential at least about 100 mV more negative than that of Cu(II).

11. The zerovalent copper species of claim 1 wherein the alkali metal salt of an aromatic anion is selected from the group consisting of lithium salts of naphthalenide, biphenylide, or anthracenylide.

* * * * *

UNITED STATES PATENT AND TRADEMARK OFFICE
CERTIFICATE OF CORRECTION

PATENT NO. : 5,490,952

DATED : February 13, 1996

INVENTOR(S) : Reuben D. Rieke

It is certified that error appears in the above-identified patent and that said Letters Patent is hereby corrected as shown below:

On column 29, line 51, please insert --ethyl-- after the word "and"

Signed and Sealed this

Tenth Day of September, 1996

Attest:

BRUCE LEHMAN

*Attesting Officer*  Commissioner of Patents and Trademarks